US012297460B1

(12) United States Patent
Daich

(10) Patent No.: US 12,297,460 B1
(45) Date of Patent: May 13, 2025

(54) VIRAL PREPARATIONS AND METHODS FOR TREATING AND MODULATING MITOCHONDRIAL EFFECTS OF CORONAVIRUS INFECTIONS

(71) Applicant: Julian Daich, Tel Aviv (IL)

(72) Inventor: Julian Daich, Tel Aviv (IL)

( * ) Notice: Subject to any disclaimer, the term of this patent is extended or adjusted under 35 U.S.C. 154(b) by 0 days.

(21) Appl. No.: 17/368,994

(22) Filed: Jul. 7, 2021

Related U.S. Application Data

(60) Provisional application No. 63/049,125, filed on Jul. 8, 2020.

(51) Int. Cl.

| | |
|---|---|
| ***A61K 39/215*** | (2006.01) |
| ***A61K 49/00*** | (2006.01) |
| ***C12N 7/00*** | (2006.01) |
| *A61K 39/00* | (2006.01) |

(52) U.S. Cl.
CPC .............. *C12N 7/00* (2013.01); *A61K 39/215* (2013.01); *A61K 49/0008* (2013.01); *A61K 2039/5254* (2013.01); *C12N 2770/20021* (2013.01); *C12N 2770/20034* (2013.01)

(58) Field of Classification Search
CPC ... A61K 39/215; A61K 2039/53; A61P 27/02; A61P 31/14; G01N 2333/165; G01N 33/56983; G01N 33/5079; C12Q 2600/158; C12Q 1/6886; C12Q 1/156; C12Q 1/158; C12Y 207/10002; C12N 2770/20034
See application file for complete search history.

(56) References Cited

PUBLICATIONS

Chen, et al. Journal of Infectious Diseases, (Aug. 1, 2007) vol. 196, No. 3, pp. 405-415.*
Liu et al. Nature Communications, Jul. 27, 2022)13:4337, pp. 1-14.*
Silver et al. Journal of Virology, Sep. 2021 vol. 95 Issue 17, pp. 1-14.*
Stewart et al. iScience 26, Nov. 27, 2023, pp. 1-35.*
He,R., Dobie,F., Ballantine,M., Leeson,A., Li.Y., Bastien,N., Cutts,T., Andonov,A., Cao,J., Booth,T.F., Plummer,F.A., Tyler,S., Baker,L. and Li,X. BCCA Genome Sciences Centre, British Columbia Centre for Disease Control and National Microbiology Laboratory Canada. Analysis of multimerization of the SARS coronavirus nucleocapsid protein. Biochem. Biophys. Res. Commun. 316 (2), 476-483 (2004).
Graham,R.L., Deming,D.J., Deming,M.E., Yount,B.L. and Baric,R. S. Evaluation of a recombination-resistant coronavirus as a broadly applicable, rapidly implementable vaccine platform. Commun Biol 1, 179 (2018).
The Chinese SARS Molecular Epidemiology Consortium. Molecular Evolution of the SARS Coronavirus During the Course of the SARS Epidemic in China; 1666 (2004):303 Science. DOI: 10.1126/science.1092002.
Li, X., Hou, P., Ma, W. et al. SARS-CoV-2 ORF10 suppresses the antiviral innate immune response by degrading MAVS through mitophagy. Cell Mol Immunol 19, 67-78 (2022). https://doi.org/10.1038/s41423-021-00807-4.
Han, L., Zhuang, M.W., Deng, J., Zheng, Y., Zhang, J., Nan, M.L., Zhang, X.J., Gao, C., and Wang, P.H. (2021). SARS-CoV-2 ORF9b antagonizes type I and III interferons by targeting multiple components of the RIG-I/ MDA-5-MAVS, TLR3-TRIF, and cGAS-STING signaling pathways. J. Med. Virol. 93, 5376-5389. https://doi.org/10.1002/jmv.27050.
Firth, A.E. (2020). A putative new SARS-CoV protein, 3c, encoded in an ORF overlapping ORF3a. J. Gen. Virol. 101, 1085-1089. https://doi.org/10.1099/jgv.0.001469Firth, A.E. (2020). A putative new SARS-CoV protein, 3c, encoded in an ORF overlappingORF3a. J. Gen. Virol. 101, 1085-1089. https://doi.org/10.1099/jgv.0.001469.
Firth, A.E. (2020). A putative new SARS-CoV protein, 3c, encoded in an ORF overlapping ORF3a. J. Gen. Virol. 101, 1085-1089. https://doi.org/10.1099/jgv.0.001469.
Stewart H, Lu Y, O'Keefe S, Valpadashi A, Cruz-Zaragoza LD, Michel HA, Nguyen SK, Carnell GW, Lukhovitskaya N, Milligan R, Adewusi Y, Jungreis I, Lulla V, Matthews DA, High S, Rehling P, Emmott E, Heeney JL, Davidson AD, Edgar Jr, Smith GL, Firth AE. The SARS-CoV-2 protein ORF3c is a mitochondrial modulator of innate immunity. iScience. Sep. 28, 2023;26(11):108080. doi: 10.1016/j.isci.2023.108080. PMID: 37860693; PMCID: PMC10583119.
Silvas JA, Vasquez DM, Park JG, Chiem K, Allué-Guardia A, Garcia-Vilanova A, Platt RN, Miorin L, Kehrer T, Cupic A, Gonzalez-Reiche AS, Bakel HV, Garcia-Sastre A, Anderson T, Torrelles JB, Ye C, Martinez-Sobrido L. Contribution of SARS-CoV-2 Accessory Proteins to Viral Pathogenicity in K18 Human ACE2 Transgenic Mice. J Virol. Aug. 10, 2021;95(17):e0040221. doi: 10.1128/JVI.00402-21. Epub Aug. 10, 2021. PMID: 34133899; PMCID: PMC8354228.
Liu, Y., Zhang, X., Liu, J. et al. A live-attenuated SARS-CoV-2 vaccine candidate with accessory protein deletions. Nat Commun 13, 4337 (2022). https://doi.org/10.1038/s41467-022-31930-z.
Harcourt,J., Tamin,A., Lu,X., Kamili,S., Sakthivel,S.K., Murray,J., Queen,K., Tao,Y., Paden,C.R., Zhang,J., Li,Y., Uehara,A., Wang,H., Goldsmith,C., Bullock,H.A., Wang,L., Whitaker,B., Lynch,B. ,Gautam,R., Schindewolf,C., Lokugamage,K.G., Scharton,D.,Plante,J. A., Mirchandani,D., Widen,S.G., Narayanan,K., Makino,S., Ksiazek,T. G., Plante,K.S., Weaver,S.C., Lindstrom,S., Tong, S., Menachery,V. D. and Thornburg,N.J. https://www.ncbi.nlm.nih.gov/nuccore/MN985325.
https://ourworldindata.org/grapher/total-covid-deaths-per-million.
(Continued)

*Primary Examiner* — Bao Q Li

(57) ABSTRACT

Attenuate coronavirus species that are able to fully replicate and spread are proposed together with the methods of obtaining thereof. The proposed coronavirus species are intended to treat and prevent viral infections including all those caused by coronavirus species that affect humans as the COVID-19 caused by the SARS-CoV2. Compared with other treatment or vaccine alternatives, the availability of such attenuate coronavirus species does not require of significant distribution and production resources.
Some of the embodiments of the invention involve the use of the attenuate coronavirus species in formulations or compositions that have to be approved as safe and effective for therapeutic use in specific territories by a valid regulatory agency as the Food and Drug Agency (FDA) in the United States.

15 Claims, 9 Drawing Sheets

Specification includes a Sequence Listing.

(56) References Cited

PUBLICATIONS

Haijema BJ, Volders H, Rottier PJ. Live, attenuated coronavirus vaccines through the directed deletion of group-specific genes provide protection against feline infectious peritonitis. J Virol. 2004;78(8):3863-3871. doi:10.1128/jvi.78.8.3863-3871.2004.
https://www.eupedia.com/europe/maps_mtdna_haplogroups.shtml.
Shi CS, Qi HY, Boularan C, et al. SARS-coronavirus open reading frame-9b suppresses innate immunity by targeting mitochondria and the MAVS/TRAF3/TRAF6 signalosome. J Immunol. 2014;193(6):3080-3089. doi:10.4049/jimmunol.1303196.
Freundt EC, Yu L, Goldsmith CS, et al. The open reading frame 3a protein of severe acute respiratory syndrome-associated coronavirus promotes membrane rearrangement and cell death. J Virol. 2010;84(2):1097-1109. doi:10.1128/JVI.01662-09.
Woelfel R, Corman VM, Guggemos W, Seilmaier M, Zange S, Mueller MA, et al. Clinical presentation and virological assessment of hospitalized cases of coronavirusdisease 2019 in a travel-associated transmission cluster. MedRxiv. 2020:2020.03.05.20030502.
Zhao J, Yuan Q, Wang H, Liu W, Liao X, Su Y, et al. Antibody responses to SARS-CoV-2 in patients of novel coronavirus disease 2019. medRxiv. 2020:2020.03.02.20030189.
Okba NMA, Muller MA, Li W, Wang C, Geurtsvankessel CH, Corman VM, et al. SARS-CoV-2 specific antibody responses in COVID-19 patients. MedRxiv. 2020:2020.03.18.20038059.
Liu W, Liu L, Kou G, Zheng Y, Ding Y, Ni W, et al. Evaluation of Nucleocapsid and Spike Protein-based ELISAs for detecting antibodies against SARS-CoV-2. MedRxiv. 2020:2020.03.16.20035014.
Long Q-X, Deng H-J, Chen J, Hu J, Liu B-Z, Liao P, et al. Antibody responses to SARS-CoV-2 in COVID-19 patients: the perspective application of serological tests in clinical practice. MedRxiv. 2020:2020.03.18.20038018.
Wan WY, Lim SH, Seng EH. Cross-reaction of sera from COVID-19 patients with SARS-CoV assays. MedRxiv. 2020:2020.03.17.20034454.
Zhao J, Yuan Q, Wang H, Liu W, Liao X, Su Y, et al. Antibody responses to SARS-CoV-2 in patients of novel coronavirus disease 2019. Clinical Infectious Diseases. 2020.
Kellamp, Barclay W. The dynamics of humoral immune responses following SARS-CoV-2 infection and the potential for reinfection. The Journal of general virology. May 20, 2020.
Xiao AT, Gao C, Zhang S. Profile of specific antibodies to SARS-CoV-2: The first report. The Journal of infection. Mar. 21, 2020.
Wu L-P, Wang N-C, Chang Y-H, Tian X-Y, Na D-Y, Zhang L-Y, et al. Duration of antibody responses after severe acute respiratory syndrome. Emerging infectious diseases. 2007;13(10):1562-4.
Callow KA, Parry HF, Sergeant M, Tyrrell DA. The time course of the immune response to experimental coronavirus infection of man. Epidemiol Infect. 1990;105(2):435-46.
Neil M Ferguson, Daniel Laydon. Gemma Nedjati-Gilani, Natsuko Imai, Kylie Ainsue, Marc Baguelin, et al. Impact of non-pharmaceutical interventions (NPIs) to reduce COVID19 mortality and healthcare demand: Imperial College; 2020 [updated Mar. 16, 2020; cited 2020 Mar. 23, 2020]. Available from: https://www.imperial.ac.uk/media/imperial-college/medicine/sph/ide/gida-fellowships/Imperial-College-COVID19-NPI-modelling-16-03-2020.pdf.
Edridge AW, Kaczorowska JM, Hoste AC, Bakker M, Klein M, Jebbink MF, et al. Human coronavirus reinfection dynamics: lessons for SARS-CoV-2. MedRxiv. 2020:2020.05.11.20086439.
Ao L, Deng W, Gao H, Xiao C, Liu J, Xue J, et al. Reinfection could not occur in SARS-CoV-2 infected rhesus macaques. BioRxiv. 2020:2020.03.13.99022.
Hu B, Zeng LP, Yang XL, Ge XY, Zhang W, et al. (2017) Discovery of a rich gene pool of bat SARS-related coronaviruses provides new insights into the origin of SARS coronavirus. PLOS Pathogens 13(11): e1006698. https://doi.org/10.1371/journal.ppat.1006698.
Yount B, Roberts RS, Sims AC, et al. Severe acute respiratory syndrome coronavirus group-specific open reading frames encode nonessential functions for replication in cell cultures and mice. J Virol. 2005;79(23):14909-14922. doi:10.1128/JVI.79.23.14909-14922.2005.
Wu, F., Zhao, S., Yu, B. et al. A new coronavirus associated with human respiratory disease in China. Nature 579, 265-269 (2020). https://doi.org/10.1038/s41586-020-2008-3.
Yvonne CF Su, Danielle E Anderson, Barnaby E Young, Feng Zhu, Martin Linster. Shirin Kalimuddin, Jenny GH Low, Zhuang Yan, Jayanthi Jayakumar, Louisa Sun, Gabriel Z Yan, Ian H Mendenhall, Yee-Sin Leo, David Chien Lye, Lin-Fa Wang, Gavin JD Smith. Discovery of a 382-nt deletion during the early evolution of SARS-CoV-2. doi: https://doi.org/10.1101/2020.03.11.987222.
Guan Y, Zheng BJ, He YQ, et al. Isolation and characterization of viruses related to the SARS coronavirus from animals in southern China. Science. 2003;302(5643):276-278. doi:10.1126/science.1087139.
Bharti SK, Sommers JA, Zhou J, et al. DNA sequences proximal to human mitochondrial DNA deletion breakpoints prevalent in human disease form G-quadruplexes, a class of DNA structures inefficiently unwound by the mitochondrial replicative Twinkle helicase. J Biol Chem. 2014;289(43):29975-29993. doi:10.1074/jbc.M114.567073.
Abudayyeh OO, Gootenberg JS, Konermann S, et al. C2c2 is a single-component programmable RNA-guided RNA-targeting CRISPR effector. Science. 2016;353(6299):aaf5573. doi:10.1126/science.aaf5573.
Zhou P, Yang XL, Wang XG, et al. A pneumonia outbreak associated with a new coronavirus of probable bat origin. Nature. 2020;579(7798):270-273. doi:10.1038/s41586-020-2012-7.
Xiao K, Zhai J, Feng Y, et al. Isolation of SARS-CoV-2-related coronavirus from Malayan pangolins [published online ahead of print, May 7, 2020]. Nature. 2020;10.1038/s41586-020-2313-x. doi:10.1038/s41586-020-2313-x.

* cited by examiner

MDPNQTNVVPPALHLVDPQIQLTITRMEDAMGQGQNSADPKVY
PIILRLGSQLSLSMARRNLDSLEARAFQSTPIVVQMTKLATTEELP
DEFVVVTAK

205

MDPKISEMHPALRLVDPQIQLAVTRMENAVGRDQNNVGPKVYPI
ILRLGSPLSLNMARKLNSLEDKAFQLTPIAVQMTKLATTEELPDE
FVVVTVK

300

301

ATGTCTGATAAT<u>G</u>GACCCCAATCAAACCAACGTAGTGCCCCCCGCATTACATTTGGTGGACCCAC
AGATTCAACTGACAATAACCAGAATGGAGGACGCAATGGGGCAAGGCCAAAACAGCGCCGACCC
CAAGGTTTACCCAATAATACTGCGTCTTGGTTCACAGCTCTCACTCAGCATGGCAAGGAGGAACT
TAGATTCCCTCGAGGCCAGGGCGTTCCAATCAACACCAATAGTGGTCCAGATGACCAAATTGGCT
ACTACCGAAGAGCTACCCGACGAGTTCGTGGTGGTGACGGCAAAATGAAAGAGCTCAGCCCCAG
ATGGTACTTCTATTACCTAGGAACTGGCCCAGAAGCTTCACTTCCCTACGGCGCTAACAAAGAAG
GCATCGTATGGGTTGCAACTGAGGGAGCCTTGAATACACCCAAAGACCACATTGGCACCCGCAAT
CCTAATAACAATGCTGCCACCGTGCTACAACTTCCTCAAGGAACAACATTGCCAAAAGGCTTCTAC
GCAGAGGGAAGCAGAGGCGGCAGTCAAGCCTCTTCTCGCTCCTCATCACGTAGTCGCGGTAATT
CAAGAAATTCAACTCCTGGCAGCAGTAGGGGAAATTCTCCTGCTCGAATGGCTAGCGGAGGTGG
TGAAACTGCCCTCGCGCTATTGCTGCTAGACAGATTGAACCAGCTTGAGAGCAAAGTTTCTGGTA
AAGGCCAACAACAACAAGGCCAAACTGTCACTAAGAAATCTGCTGCTGAGGCATCTAAAAAGCCT
CGCCAAAAACGTACTGCCACAAAACAGTACAACGTCACTCAAGCATTTGGGAGACGTGGTCCAG
AACAAACCCAAGGAAATTTCGGGGACCAAGACCTAATCAGACAAGGAACTGATTACAAACATTGG
CCGCAAATTGCACAATTTGCTCCAAGTGCCTCTGCATTCTTTGGAATGTCACGCATTGGCATGGA
AGTCACACCTTCGGGAACATGGCTGACTTATCATGGAGCCATTAAATTGGATGACAAAGATCCACA
ATTCAAAGACAACGTCATACTGCTGAACAAGCACATTGACGCATACAAAACATTCCCACCAACAGA
GCCTAAAAAGGACAAAAAGAAAAAGACTGATGAAGCTCAGCCTTTGCCGCAGAGACAAAAGAAG
CAGCCCACTGTGACTCTTCTTCCTGCGGCTGACATGGATGATTTCTCCAGACAACTTCAAAATTCC
ATGAGTGGAGCTTCTGCTGATTCAACTCAGGCATAA

302

ATGTCTGATAAT<u>C</u>GACCCCAATCAAACCAACGTAGTGCCCCCCGCATTACATTTGGTGGACCCAC
AGATTCAACTGACAATAACCAGAATGGAGGACGCAATGGGGCAAGGCCAAAACAGCGCCGACCC
CAAGGTTTACCCAATAATACTGCGTCTTGGTTCACAGCTCTCACTCAGCATGGCAAGGAGGAACT
TAGATTCCCTCGAGGCCAGGGCGTTCCAATCAACACCAATAGTGGTCCAGATGACCAAATTGGCT
ACTACCGAAGAGCTACCCGACGAGTTCGTGGTGGTGACGGCAAAATGAAAGAGCTCAGCCCCAG
ATGGTACTTCTATTACCTAGGAACTGGCCCAGAAGCTTCACTTCCCTACGGCGCTAACAAAGAAG
GCATCGTATGGGTTGCAACTGAGGGAGCCTTGAATACACCCAAAGACCACATTGGCACCCGCAAT
CCTAATAACAATGCTGCCACCGTGCTACAACTTCCTCAAGGAACAACATTGCCAAAAGGCTTCTAC
GCAGAGGGAAGCAGAGGCGGCAGTCAAGCCTCTTCTCGCTCCTCATCACGTAGTCGCGGTAATT
CAAGAAATTCAACTCCTGGCAGCAGTAGGGGAAATTCTCCTGCTCGAATGGCTAGCGGAGGTGG
TGAAACTGCCCTCGCGCTATTGCTGCTAGACAGATTGAACCAGCTTGAGAGCAAAGTTTCTGGTA
AAGGCCAACAACAACAAGGCCAAACTGTCACTAAGAAATCTGCTGCTGAGGCATCTAAAAAGCCT
CGCCAAAAACGTACTGCCACAAAACAGTACAACGTCACTCAAGCATTTGGGAGACGTGGTCCAG
AACAAACCCAAGGAAATTTCGGGGACCAAGACCTAATCAGACAAGGAACTGATTACAAACATTGG
CCGCAAATTGCACAATTTGCTCCAAGTGCCTCTGCATTCTTTGGAATGTCACGCATTGGCATGGA
AGTCACACCTTCGGGAACATGGCTGACTTATCATGGAGCCATTAAATTGGATGACAAAGATCCACA
ATTCAAAGACAACGTCATACTGCTGAACAAGCACATTGACGCATACAAAACATTCCCACCAACAGA
GCCTAAAAAGGACAAAAAGAAAAAGACTGATGAAGCTCAGCCTTTGCCGCAGAGACAAAAGAAG
CAGCCCACTGTGACTCTTCTTCCTGCGGCTGACATGGATGATTTCTCCAGACAACTTCAAAATTCC
ATGAGTGGAGCTTCTGCTGATTCAACTCAGGCATAA

Fig. 3

SARS-CoV2 gene N

400

401

ATGTCTGATAAATGGACCCCAAAATCAGCGAAATGCACCCCGCATTACGTTTGGTGGACCC
TCAGATTCAACTGGCAGTAACCAGAATGGAGAACGCAGTGGGGCGCGATCAAAACAACG
TCGGCCCCAAGGTTTACCCAATAATACTGCGTCTTGGTTCACCGCTCTCACTCAACATGG
CAAGGAAGACCTTAAATTCCCTCGAGGACAAGGCGTTCCAATTAACACCAATAGCAGTCC
AGATGACCAAATTGGCTACTACCGAAGAGCTACCAGACGAATTCGTGGTGGTGACGGTA
AAATGAAAGATCTCAGTCCAAGATGGTATTTCTACTACCTAGGAACTGGGCCAGAAGCTG
GACTTCCCTATGGTGCTAACAAAGACGGCATCATATGGGTTGCAACTGAGGGAGCCTTG
AATACACCAAAAGATCACATTGGCACCCGCAATCCTGCTAACAATGCTGCAATCGTGCTA
CAACTTCCTCAAGGAACAACATTGCCAAAAGGCTTCTACGCAGAAGGGAGCAGAGGCG
GCAGTCAAGCCTCTTCTCGTTCCTCATCACGTAGTCGCAACAGTTCAAGAAATTCAACTC
CAGGCAGCAGTAGGGGAACTTCTCCTGCTAGAATGGCTGGCAATGGCGGTGATGCTGCT
CTTGCTTTGCTGCTGCTTGACAGATTGAACCAGCTTGAGAGCAAAATGTCTGGTAAAGGC
CAACAACAACAAGGCCAAACTGTCACTAAGAAATCTGCTGCTGAGGCTTCTAAGAAGCCT
CGGCAAAAACGTACTGCCACTAAAGCATACAATGTAACACAAGCTTTTGGCAGACGTGGT
CCAGAACAAACCCAAGGAAATTTTGGGGACCAGGAACTAATCAGACAAGGAACTGATTA
CAAACATTGGCCGCAAATTGCACAATTTGCCCCCAGCGCTTCAGCGTTCTTCGGAATGTC
GCGCATTGGCATGGAAGTCACACCTTCGGGAACGTGGTTGACCTACACAGGTGCCATCA
AATTGGATGACAAAGATCCAAATTTCAAAGATCAAGTCATTTTGCTGAATAAGCATATTGAC
GCATACAAAACATTCCCACCAACAGAGCCTAAAAAGGACAAAAAGAAGAAGGCTGATGAA
ACTCAAGCCTTACCGCAGAGACAGAAGAAACAGCAAACTGTGACTCTTCTTCCTGCTGC
AGATTTGGATGATTTCTCCAAACAATTGCAACAATCCATGAGCAGTGCTGACTCAACTCA
GGCCTAA

402

ATGTCTGATAAATCGACCCCAAAATCAGCGAAATGCACCCCGCATTACGTTTGGTGGACCC
TCAGATTCAACTGGCAGTAACCAGAATGGAGAACGCAGTGGGGCGCGATCAAAACAACG
TCGGCCCCAAGGTTTACCCAATAATACTGCGTCTTGGTTCACCGCTCTCACTCAACATGG
CAAGGAAGACCTTAAATTCCCTCGAGGACAAGGCGTTCCAATTAACACCAATAGCAGTCC
AGATGACCAAATTGGCTACTACCGAAGAGCTACCAGACGAATTCGTGGTGGTGACGGTA
AAATGAAAGATCTCAGTCCAAGATGGTATTTCTACTACCTAGGAACTGGGCCAGAAGCTG
GACTTCCCTATGGTGCTAACAAAGACGGCATCATATGGGTTGCAACTGAGGGAGCCTTG
AATACACCAAAAGATCACATTGGCACCCGCAATCCTGCTAACAATGCTGCAATCGTGCTA
CAACTTCCTCAAGGAACAACATTGCCAAAAGGCTTCTACGCAGAAGGGAGCAGAGGCG
GCAGTCAAGCCTCTTCTCGTTCCTCATCACGTAGTCGCAACAGTTCAAGAAATTCAACTC
CAGGCAGCAGTAGGGGAACTTCTCCTGCTAGAATGGCTGGCAATGGCGGTGATGCTGCT
CTTGCTTTGCTGCTGCTTGACAGATTGAACCAGCTTGAGAGCAAAATGTCTGGTAAAGGC
CAACAACAACAAGGCCAAACTGTCACTAAGAAATCTGCTGCTGAGGCTTCTAAGAAGCCT
CGGCAAAAACGTACTGCCACTAAAGCATACAATGTAACACAAGCTTTTGGCAGACGTGGT
CCAGAACAAACCCAAGGAAATTTTGGGGACCAGGAACTAATCAGACAAGGAACTGATTA
CAAACATTGGCCGCAAATTGCACAATTTGCCCCCAGCGCTTCAGCGTTCTTCGGAATGTC
GCGCATTGGCATGGAAGTCACACCTTCGGGAACGTGGTTGACCTACACAGGTGCCATCA
AATTGGATGACAAAGATCCAAATTTCAAAGATCAAGTCATTTTGCTGAATAAGCATATTGAC
GCATACAAAACATTCCCACCAACAGAGCCTAAAAAGGACAAAAAGAAGAAGGCTGATGAA
ACTCAAGCCTTACCGCAGAGACAGAAGAAACAGCAAACTGTGACTCTTCTTCCTGCTGC
AGATTTGGATGATTTCTCCAAACAATTGCAACAATCCATGAGCAGTGCTGACTCAACTCA
GGCCTAA

MGYINVFAFPFTIYSLLLCRMNSRNYIAQVDVVNFNLT

500b

505

**AT*G***GGCTATATAAACGTTTTCGCTTTTCCGTTTACGATATATAGTCTACTCTTGTGCAGAAT
GAATTCTCGTAACTACATAGCACAAGTAGATGTAGTTAACTTTAATCTCACATA

506

**AT*C***GGCTATATAAACGTTTTCGCTTTTCCGTTTACGATATATAGTCTACTCTTGTGCAGAAT
GAATTCTCGTAACTACATAGCACAAGTAGATGTAGTTAACTTTAATCTCACATA

```
                                    ┌─────────────┐
                                 610│ Existing CoV│
                                    │   species   │
                                    └──────┬──────┘
                                           │
                                           ▼
                                    ╱─────────────╲
                                 620╱ A candidate  ╲
                                   ╱ protein from   ╲
                                  ╱  the CoV genome/ ╲
                                  ╲  proteome that    ╱
                                   ╲affecting         ╱
                                    ╲mitochondrial   ╱
                                     ╲function      ╱
                                      ╲is identified╱
                                       ╲───────────╱
```

600

630 The method is discarded

640 Removal/ silencing of the protein by gene editing

650 Obtaining a new CoV without the protein

660 Is the effect on mitochondrial function suppressed?

670 Can the edited CoV replicate and infect?

680 Is there an alternative gene editing strategy available?

690 Changing the gene editing strategy

695 The protein is discarded as candidate

699 Attenuated new CoV obtained

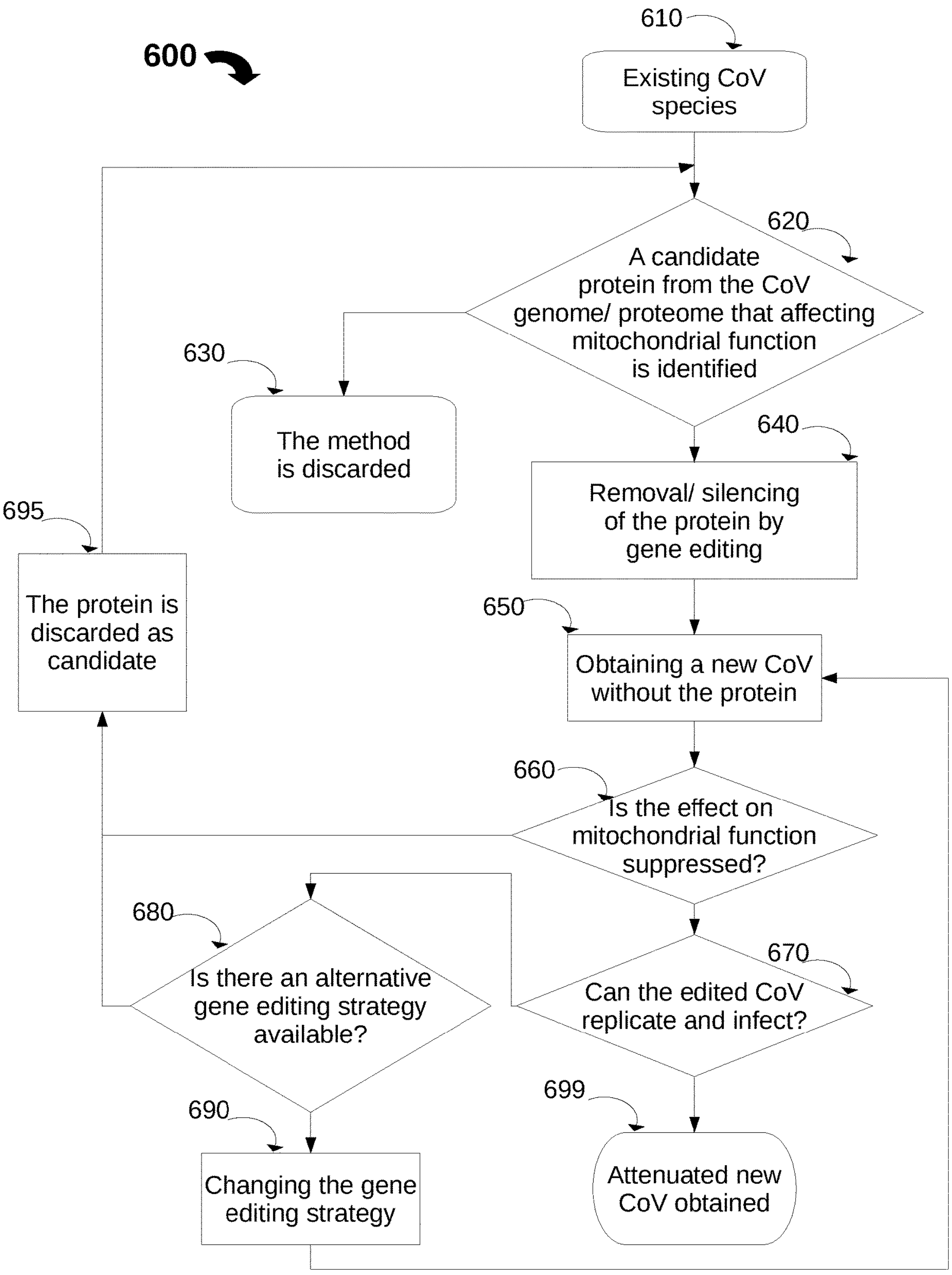

Fig. 6

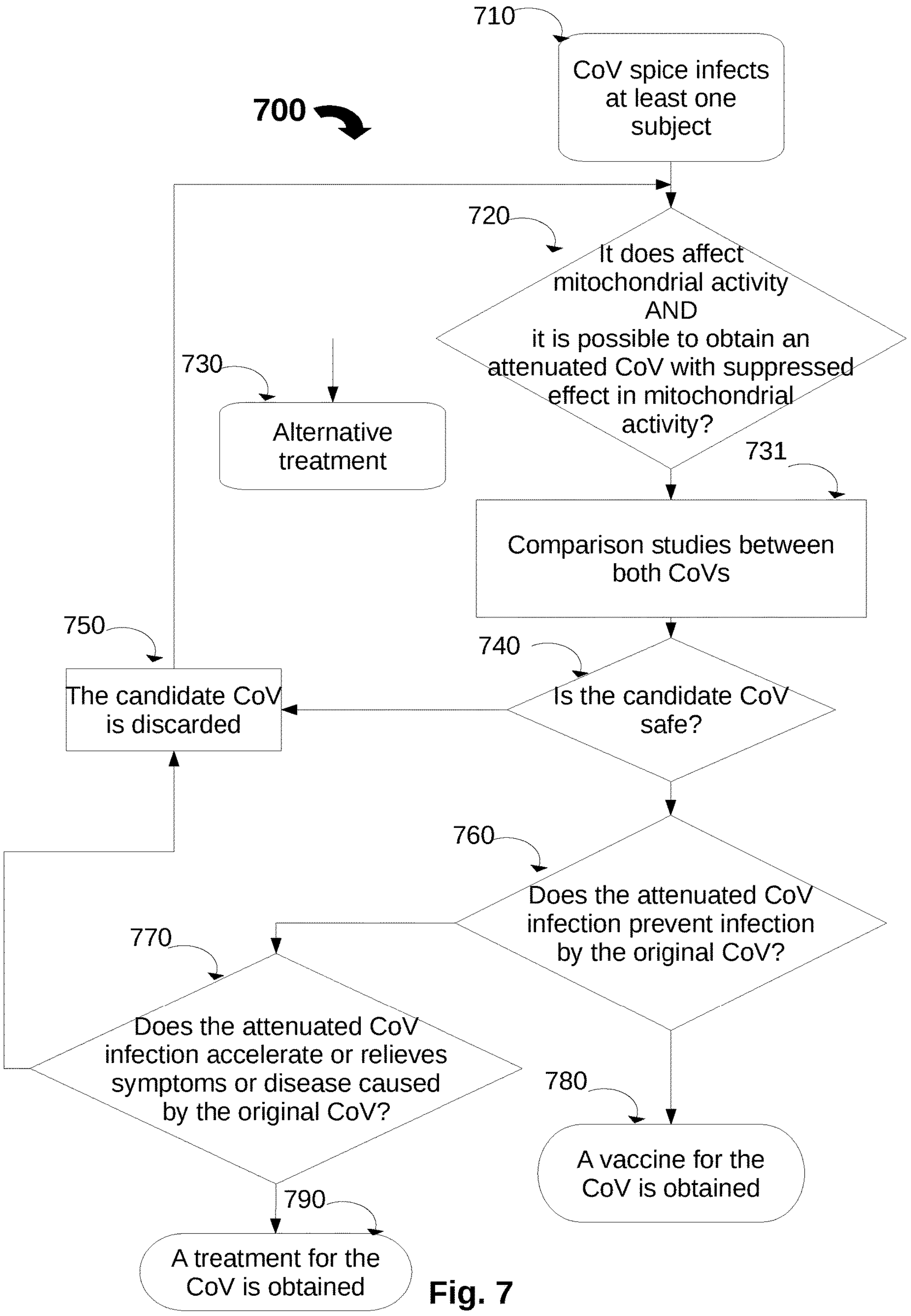

Fig. 7

```
                                    710
                                     ↓
                           ┌──────────────────┐
                           │  CoV spice infects│
      700                  │   at least one    │
                           │     subject       │
                           └──────────────────┘
                                     ↓
                          720
                                 ╱ It does affect ╲
                                ╱ mitochondrial activity ╲
                               ╱         AND              ╲
       730                    ╱  it is possible to obtain an ╲
         ↓                   ╱ attenuated CoV with suppressed ╲
   ┌───────────┐              ╲    effect in mitochondrial    ╱
   │Alternative│               ╲        activity?           ╱
   │ treatment │                ╲                         ╱  731
   └───────────┘                                             ↓
                                                  ┌──────────────────┐
                                                  │Comparison studies between│
    750                                           │      both CoVs          │
     ↓                          740               └──────────────────┘
┌──────────────┐                 ↓                         ↓
│The candidate CoV│◄──────── ╱ Is the candidate CoV ╲
│ is discarded │              ╲      safe?         ╱
└──────────────┘                      ↓
                              760
                                ↓
                       ╱ Does the attenuated CoV ╲
                      ╱  infection prevent infection ╲
         770         ╲   by the original CoV?      ╱
          ↓
  ╱ Does the attenuated CoV ╲
 ╱ infection accelerate or relieves╲    780
 ╲ symptoms or disease caused    ╱    ↓
  ╲   by the original CoV?     ╱   ┌──────────────┐
                                   │A vaccine for the│
                      790          │ CoV is obtained │
                       ↓           └──────────────┘
              ┌──────────────┐
              │A treatment for the│  Fig. 7
              │ CoV is obtained │
              └──────────────┘
```

810 — A CoV is designed as a weapon

800

820 — It does affect mitochondrial activity AND it is possible to obtain an attenuated CoV with suppressed effect in mitochondrial activity?

830 — Alternative treatment

831 — Comparison studies between both CoVs

840 — Is the obtained CoV safe?

850 — The obtained CoV is discarded

860 — Does the attenuated CoV infection accelerate or relieves symptoms or disease caused by the original CoV?

870 — Does the attenuated CoV infection prevent infection by the original CoV?

880 — A antidote for the weapon is obtained

890 — A vaccine for the weapon is obtained

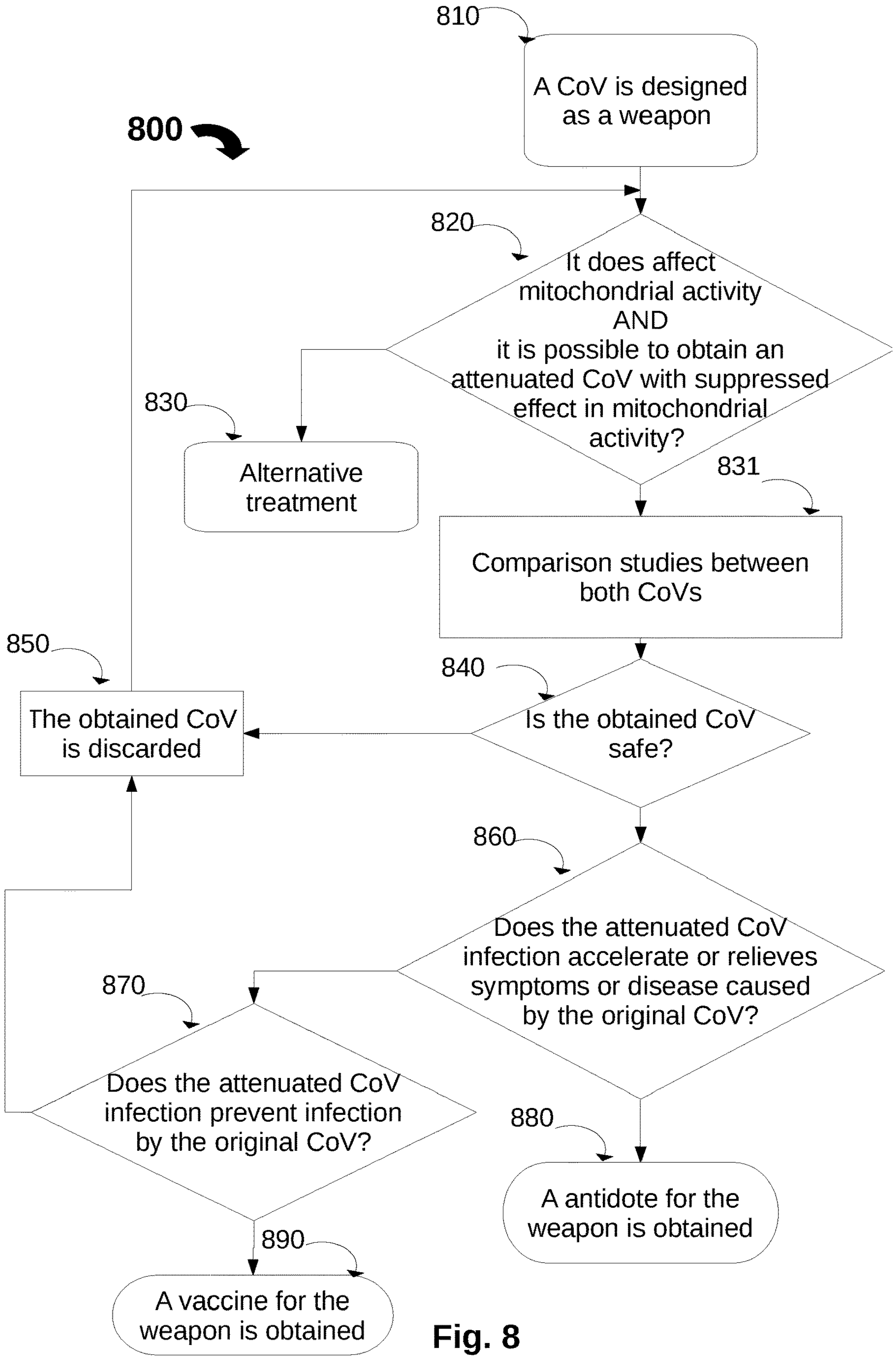

Fig. 8

900
910
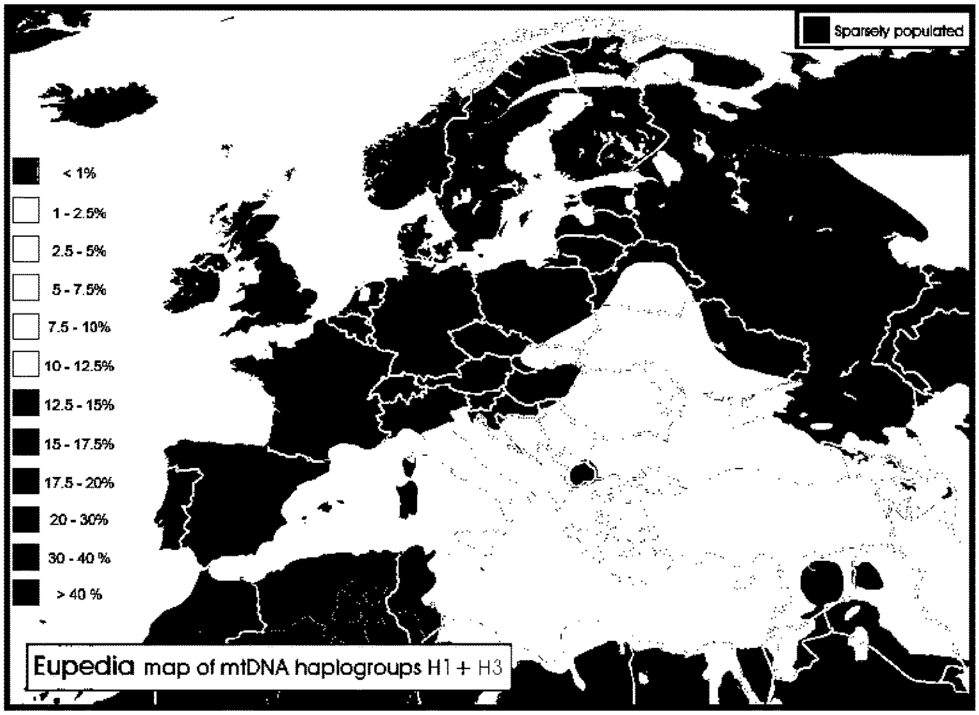
920
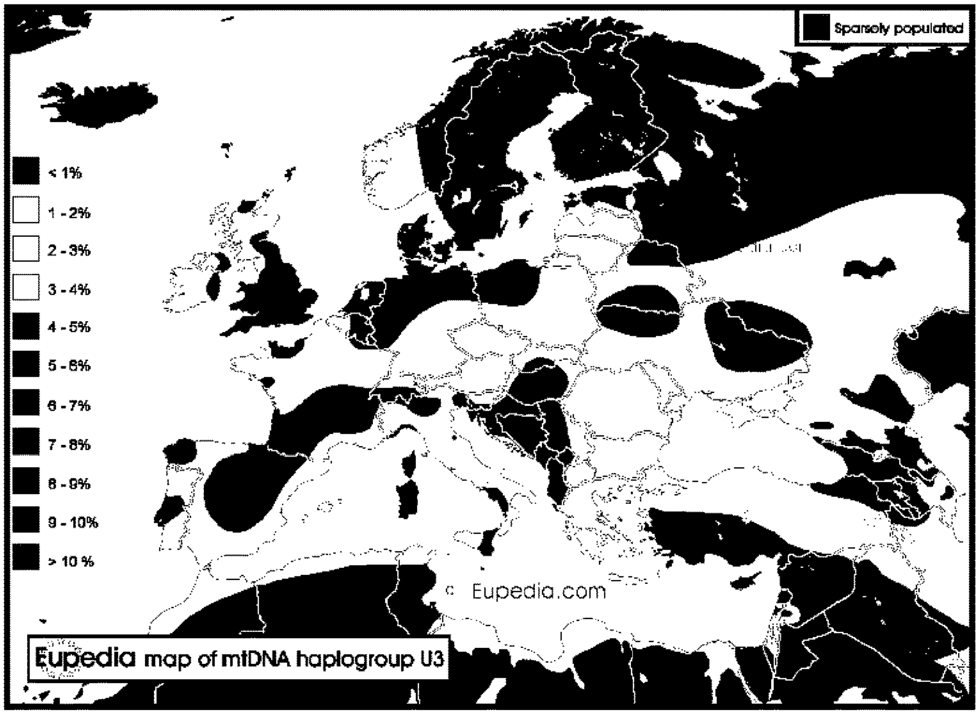
Fig. 9

SEQUENCE LISTING

```
<160> NUMBER OF SEQ ID NOS: 25

<210> SEQ ID NO 1
<211> LENGTH: 1269
<212> TYPE: RNA
<213> ORGANISM: Artificial Sequence
<220> FEATURE:
<223> OTHER INFORMATION: Edited N gene from SARS CoV

<400> SEQUENCE: 1

atgtctgata atcgacccca atcaaaccaa cgtagtgccc cccgcattac atttggtgga     60

cccacagatt caactgacaa taaccagaat ggaggacgca atggggcaag gccaaaacag    120

cgccgacccc aaggtttacc caataatact gcgtcttggt tcacagctct cactcagcat    180

ggcaaggagg aacttagatt ccctcgaggc cagggcgttc caatcaacac caatagtggt    240

ccagatgacc aaattggcta ctaccgaaga gctacccgac gagttcgtgg tggtgacggc    300

aaaatgaaag agctcagccc cagatggtac ttctattacc taggaactgg cccagaagct    360

tcacttccct acggcgctaa caaagaaggc atcgtatggg ttgcaactga gggagccttg    420
```

-continued

```
aatacaccca aagaccacat tggcacccgc aatcctaata acaatgctgc caccgtgcta     480

caacttcctc aaggaacaac attgccaaaa ggcttctacg cagagggaag cagaggcggc     540

agtcaagcct cttctcgctc ctcatcacgt agtcgcggta attcaagaaa ttcaactcct     600

ggcagcagta ggggaaattc tcctgctcga atggctagcg gaggtggtga aactgccctc     660

gcgctattgc tgctagacag attgaaccag cttgagagca aagtttctgg taaaggccaa     720

caacaacaag gccaaactgt cactaagaaa tctgctgctg aggcatctaa aaagcctcgc     780

caaaaacgta ctgccacaaa acagtacaac gtcactcaag catttgggag acgtggtcca     840

gaacaaaccc aaggaaattt cggggaccaa gacctaatca gacaaggaac tgattacaaa     900

cattggccgc aaattgcaca atttgctcca agtgcctctg cattctttgg aatgtcacgc     960

attggcatgg aagtcacacc ttcgggaaca tggctgactt atcatggagc cattaaattg    1020

gatgacaaag atccacaatt caaagacaac gtcatactgc tgaacaagca cattgacgca    1080

tacaaaacat tcccaccaac agagcctaaa aaggacaaaa agaaaaagac tgatgaagct    1140

cagcctttgc cgcagagaca aaagaagcag cccactgtga ctcttcttcc tgcggctgac    1200

atggatgatt tctccagaca acttcaaaat tccatgagtg gagcttctgc tgattcaact    1260

caggcataa                                                            1269
```

```
<210> SEQ ID NO 2
<211> LENGTH: 1260
<212> TYPE: RNA
<213> ORGANISM: Artificial Sequence
<220> FEATURE:
<223> OTHER INFORMATION: Edited gene N from SARS CoV 2

<400> SEQUENCE: 2
```

```
atgtctgata atcgacccca aaatcagcga aatgcacccc gcattacgtt tggtggaccc      60

tcagattcaa ctggcagtaa ccagaatgga gaacgcagtg gggcgcgatc aaaacaacgt     120

cggccccaag gtttacccaa taatactgcg tcttggttca ccgctctcac tcaacatggc     180

aaggaagacc ttaaattccc tcgaggacaa ggcgttccaa ttaacaccaa tagcagtcca     240

gatgaccaaa ttggctacta ccgaagagct accagacgaa ttcgtggtgg tgacggtaaa     300

atgaaagatc tcagtccaag atggtatttc tactacctag gaactgggcc agaagctgga     360

cttccctatg gtgctaacaa agacggcatc atatgggttg caactgaggg agccttgaat     420

acaccaaaag atcacattgg cacccgcaat cctgctaaca atgctgcaat cgtgctacaa     480

cttcctcaag gaacaacatt gccaaaaggc ttctacgcag aagggagcag aggcggcagt     540

caagcctctt ctcgttcctc atcacgtagt cgcaacagtt caagaaattc aactccaggc     600

agcagtaggg gaacttctcc tgctagaatg gctggcaatg gcggtgatgc tgctcttgct     660

ttgctgctgc ttgacagatt gaaccagctt gagagcaaaa tgtctggtaa aggccaacaa     720

caacaaggcc aaactgtcac taagaaatct gctgctgagg cttctaagaa gcctcggcaa     780

aaacgtactg ccactaaagc atacaatgta acacaagctt ttggcagacg tggtccagaa     840

caaacccaag gaaattttgg ggaccaggaa ctaatcagac aaggaactga ttacaaacat     900

tggccgcaaa ttgcacaatt tgcccccagc gcttcagcgt tcttcggaat gtcgcgcatt     960

ggcatggaag tcacaccttc gggaacgtgg ttgacctaca caggtgccat caaattggat    1020

gacaaagatc caaatttcaa agatcaagtc attttgctga ataagcatat tgacgcatac    1080

aaaacattcc caccaacaga gcctaaaaag gacaaaaaga agaaggctga tgaaactcaa    1140
```

-continued gccttaccgc agagacagaa gaaacagcaa actgtgactc ttcttcctgc tgcagatttg 1200
gatgatttct ccaaacaatt gcaacaatcc atgagcagtg ctgactcaac tcaggcctaa 1260

<210> SEQ ID NO 3
<211> LENGTH: 116
<212> TYPE: RNA
<213> ORGANISM: Artificial Sequence
<220> FEATURE:
<223> OTHER INFORMATION: Edited ORF10 from SARS CoV 2

<400> SEQUENCE: 3
atcggctata taaacgtttt cgcttttccg tttacgatat atagtctact cttgtgcaga 60
atgaattctc gtaactacat agcacaagta gatgtagtta actttaatct cacata 116

<210> SEQ ID NO 4
<211> LENGTH: 49
<212> TYPE: DNA
<213> ORGANISM: Artificial Sequence
<220> FEATURE:
<223> OTHER INFORMATION: Primer Cov-T7-N-F for DNA template

<400> SEQUENCE: 4
tactgtaata cgactcacta taggatgtct gataatggac cccaaaatc 49

<210> SEQ ID NO 5
<211> LENGTH: 21
<212> TYPE: DNA
<213> ORGANISM: Artificial Sequence
<220> FEATURE:
<223> OTHER INFORMATION: Pirme polyT-N-R to produce DNA template

<400> SEQUENCE: 5
aggcctgagt tgagtcagca c 21

<210> SEQ ID NO 6
<211> LENGTH: 45
<212> TYPE: DNA
<213> ORGANISM: Artificial Sequence
<220> FEATURE:
<223> OTHER INFORMATION: Primer for the isolation of SARS A subclone

<400> SEQUENCE: 6
tactaatacg actcactata gatattaggt ttttacctac ccagg 45

<210> SEQ ID NO 7
<211> LENGTH: 20
<212> TYPE: DNA
<213> ORGANISM: Artificial Sequence
<220> FEATURE:
<223> OTHER INFORMATION: Primer for the isolation of SARS A subclone

<400> SEQUENCE: 7
acaccatagt caacgatgcc 20

<210> SEQ ID NO 8
<211> LENGTH: 23
<212> TYPE: DNA
<213> ORGANISM: Artificial Sequence
<220> FEATURE:
<223> OTHER INFORMATION: Primer for the isolation of SARS B subclone

<400> SEQUENCE: 8
gcctatatgc atggatgtta gat 23

-continued

<210> SEQ ID NO 9
<211> LENGTH: 23
<212> TYPE: DNA
<213> ORGANISM: Artificial Sequence
<220> FEATURE:
<223> OTHER INFORMATION: Primer for the isolation of SARS B subclone

<400> SEQUENCE: 9
tgaaccgcca cgctggctaa acc 23

<210> SEQ ID NO 10
<211> LENGTH: 21
<212> TYPE: DNA
<213> ORGANISM: Artificial Sequence
<220> FEATURE:
<223> OTHER INFORMATION: Primer for the isolation of SARS C subclone

<400> SEQUENCE: 10
agccagcgtg gcggttcata c 21

<210> SEQ ID NO 11
<211> LENGTH: 24
<212> TYPE: DNA
<213> ORGANISM: Artificial Sequence
<220> FEATURE:
<223> OTHER INFORMATION: Primer for the isolation of SARS C subclone

<400> SEQUENCE: 11
aggcctcttg ggcagtggca taag 24

<210> SEQ ID NO 12
<211> LENGTH: 22
<212> TYPE: DNA
<213> ORGANISM: Artificial Sequence
<220> FEATURE:
<223> OTHER INFORMATION: Primer for the isolation of SARS D subclone

<400> SEQUENCE: 12
actgcccaag atgcctatga gc 22

<210> SEQ ID NO 13
<211> LENGTH: 26
<212> TYPE: DNA
<213> ORGANISM: Artificial Sequence
<220> FEATURE:
<223> OTHER INFORMATION: Primer for the isolation of SARS D subclone

<400> SEQUENCE: 13
cagccaggag ggcagacttc acaacc 26

<210> SEQ ID NO 14
<211> LENGTH: 29
<212> TYPE: DNA
<213> ORGANISM: Artificial Sequence
<220> FEATURE:
<223> OTHER INFORMATION: Primer for the isolation of SARS E subclone

<400> SEQUENCE: 14
gtctgccctc ctggctgata agtttccag 29

<210> SEQ ID NO 15
<211> LENGTH: 22
<212> TYPE: DNA
<213> ORGANISM: Artificial Sequence
<220> FEATURE:
<223> OTHER INFORMATION: Primer for the isolation of SARS E subclone -continued

<400> SEQUENCE: 15
gagcagccgt gtaggcagca at 22

<210> SEQ ID NO 16
<211> LENGTH: 22
<212> TYPE: DNA
<213> ORGANISM: Artificial Sequence
<220> FEATURE:
<223> OTHER INFORMATION: Primer for the isolation of SARS F subclone

<400> SEQUENCE: 16
attgctgcct acacggctgc tc 22

<210> SEQ ID NO 17
<211> LENGTH: 18
<212> TYPE: DNA
<213> ORGANISM: Artificial Sequence
<220> FEATURE:
<223> OTHER INFORMATION: Primer for the isolation of SARS F subclone

<400> SEQUENCE: 17
gtcattctcc taagaagc 18

<210> SEQ ID NO 18
<211> LENGTH: 56
<212> TYPE: DNA
<213> ORGANISM: Artificial Sequence
<220> FEATURE:
<223> OTHER INFORMATION: Primer for the transcripion of SARS gene N subclone
<220> FEATURE:
<221> NAME/KEY: misc_feature
<222> LOCATION: (1)..(2)
<223> OTHER INFORMATION: n is a, c, g, or t

<400> SEQUENCE: 18
nnggcctcga tggccattta ggtgacacta tagatgtctg ataatggacc ccaatc 56

<210> SEQ ID NO 19
<211> LENGTH: 50
<212> TYPE: DNA
<213> ORGANISM: Artificial Sequence
<220> FEATURE:
<223> OTHER INFORMATION: Primer for the transcripion of SARS gene N subclone
<220> FEATURE:
<221> NAME/KEY: misc_feature
<222> LOCATION: (1)..(3)
<223> OTHER INFORMATION: n is a, c, g, or t

<400> SEQUENCE: 19
nnnttttttt ttttttttt ttttttttta tgcctgagtt gaatcagcag 50

<210> SEQ ID NO 20
<211> LENGTH: 98
<212> TYPE: PRT
<213> ORGANISM: SARS CoV

<400> SEQUENCE: 20

```
Met Asp Pro Asn Gln Thr Asn Val Val Pro Pro Ala Leu His Leu Val
1               5                   10                  15

Asp Pro Gln Ile Gln Leu Thr Ile Thr Arg Met Glu Asp Ala Met Gly
            20                  25                  30

Gln Gly Gln Asn Ser Ala Asp Pro Lys Val Tyr Pro Ile Ile Leu Arg
        35                  40                  45
```

```
Leu Gly Ser Gln Leu Ser Leu Ser Met Ala Arg Arg Asn Leu Asp Ser
    50                  55                  60

Leu Glu Ala Arg Ala Phe Gln Ser Thr Pro Ile Val Val Gln Met Thr
65                  70                  75                  80

Lys Leu Ala Thr Thr Glu Glu Leu Pro Asp Glu Phe Val Val Val Thr
                85                  90                  95

Ala Lys


<210> SEQ ID NO 21
<211> LENGTH: 96
<212> TYPE: PRT
<213> ORGANISM: SARS CoV 2

<400> SEQUENCE: 21

Met Asp Pro Lys Ile Ser Glu Met His Pro Ala Leu Arg Leu Val Asp
1               5                   10                  15

Pro Gln Ile Gln Leu Ala Val Thr Arg Met Glu Asn Ala Val Gly Arg
            20                  25                  30

Asp Gln Asn Asn Val Gly Pro Lys Val Tyr Pro Ile Ile Leu Arg Leu
        35                  40                  45

Gly Ser Pro Leu Ser Leu Asn Met Ala Arg Lys Leu Asn Ser Leu Glu
    50                  55                  60

Asp Lys Ala Phe Gln Leu Thr Pro Ile Ala Val Gln Met Thr Lys Leu
65                  70                  75                  80

Ala Thr Thr Glu Glu Leu Pro Asp Glu Phe Val Val Val Thr Val Lys
                85                  90                  95


<210> SEQ ID NO 22
<211> LENGTH: 1269
<212> TYPE: RNA
<213> ORGANISM: SARS CoV
<300> PUBLICATION INFORMATION:
<301> AUTHORS: Graham,R.L., Deming,D.J., Deming,M.E., Yount,B.L. and
      Baric,R.S.
<302> TITLE: Evaluation of a recombination-resistant coronavirus as a
      broadly applicable, rapidly implementable vaccine platform
<303> JOURNAL: Commun Biol
<304> VOLUME: 1
<306> PAGES: 179
<307> DATE: 2018-10-17
<308> DATABASE ACCESSION NUMBER: MK062184
<309> DATABASE ENTRY DATE: 2018-10-17
<313> RELEVANT RESIDUES IN SEQ ID NO: (28277)..(28573)

<400> SEQUENCE: 22

atgtctgata atggacccca atcaaaccaa cgtagtgccc cccgcattac atttggtgga      60

cccacagatt caactgacaa taaccagaat ggaggacgca atggggcaag gccaaaacag     120

cgccgacccc aaggtttacc caataatact gcgtcttggt tcacagctct cactcagcat     180

ggcaaggagg aacttagatt ccctcgaggc cagggcgttc caatcaacac caatagtggt     240

ccagatgacc aaattggcta ctaccgaaga gctacccgac gagttcgtgg tggtgacggc     300

aaaatgaaag agctcagccc cagatggtac ttctattacc taggaactgg cccagaagct     360

tcacttccct acggcgctaa caaagaaggc atcgtatggg ttgcaactga gggagccttg     420

aatacaccca aagaccacat tggcacccgc aatcctaata acaatgctgc caccgtgcta     480

caacttcctc aaggaacaac attgccaaaa ggcttctacg cagagggaag cagaggcggc     540

agtcaagcct cttctcgctc ctcatcacgt agtcgcggta attcaagaaa ttcaactcct     600

ggcagcagta ggggaaattc tcctgctcga atggctagcg gaggtggtga aactgccctc     660
```

```
gcgctattgc tgctagacag attgaaccag cttgagagca aagtttctgg taaaggccaa    720

caacaacaag gccaaactgt cactaagaaa tctgctgctg aggcatctaa aaagcctcgc    780

caaaaacgta ctgccacaaa acagtacaac gtcactcaag catttgggag acgtggtcca    840

gaacaaaccc aaggaaattt cggggaccaa gacctaatca gacaaggaac tgattacaaa    900

cattggccgc aaattgcaca atttgctcca agtgcctctg cattctttgg aatgtcacgc    960

attggcatgg aagtcacacc ttcgggaaca tggctgactt atcatggagc cattaaattg   1020

gatgacaaag atccacaatt caaagacaac gtcatactgc tgaacaagca cattgacgca   1080

tacaaaacat tcccaccaac agagcctaaa aaggacaaaa agaaaaagac tgatgaagct   1140

cagcctttgc cgcagagaca aaagaagcag cccactgtga ctcttcttcc tgcggctgac   1200

atggatgatt tctccagaca acttcaaaat tccatgagtg gagcttctgc tgattcaact   1260

caggcataa                                                           1269
```

<210> SEQ ID NO 23
<211> LENGTH: 1260
<212> TYPE: RNA
<213> ORGANISM: SARS CoV 2
<300> PUBLICATION INFORMATION:
<301> AUTHORS: Wu,F., Zhao,S., Yu,B., Chen,Y.M., Wang,W., Song,Z.G., Hu,Y.,Tao,Z.W., Tian,J.H., Pei,Y.Y., Yuan,M.L., Zhang,Y.L., Dai,F.H.,Liu,Y., Wang,Q.M., Zheng,J.J., Xu,L., Holmes,E.C. and Zhang,Y.Z
<302> TITLE: A new coronavirus associated with human respiratory disease in China
<303> JOURNAL: Nature
<304> VOLUME: 579
<305> ISSUE: 7798
<306> PAGES: 265-269
<307> DATE: 2020-02-03
<308> DATABASE ACCESSION NUMBER: NC_045512
<309> DATABASE ENTRY DATE: 2020-07-07
<313> RELEVANT RESIDUES IN SEQ ID NO: (28274)..(29534)

<400> SEQUENCE: 23

```
atgtctgata atggacccca aaatcagcga aatgcacccc gcattacgtt tggtggaccc     60

tcagattcaa ctggcagtaa ccagaatgga gaacgcagtg gggcgcgatc aaaacaacgt    120

cggccccaag gtttacccaa taatactgcg tcttggttca ccgctctcac tcaacatggc    180

aaggaagacc ttaaattccc tcgaggacaa ggcgttccaa ttaacaccaa tagcagtcca    240

gatgaccaaa ttggctacta ccgaagagct accagacgaa ttcgtggtgg tgacggtaaa    300

atgaaagatc tcagtccaag atggtatttc tactacctag gaactgggcc agaagctgga    360

cttccctatg gtgctaacaa agacggcatc atatgggttg caactgaggg agccttgaat    420

acaccaaaag atcacattgg cacccgcaat cctgctaaca atgctgcaat cgtgctacaa    480

cttcctcaag gaacaacatt gccaaaaggc ttctacgcag aagggagcag aggcggcagt    540

caagcctctt ctcgttcctc atcacgtagt cgcaacagtt caagaaattc aactccaggc    600

agcagtaggg gaacttctcc tgctagaatg gctggcaatg gcggtgatgc tgctcttgct    660

ttgctgctgc ttgacagatt gaaccagctt gagagcaaaa tgtctggtaa aggccaacaa    720

caacaaggcc aaactgtcac taagaaatct gctgctgagg cttctaagaa gcctcggcaa    780

aaacgtactg ccactaaagc atacaatgta acacaagctt ttggcagacg tggtccagaa    840

caaacccaag gaaattttgg ggaccaggaa ctaatcagac aaggaactga ttacaaacat    900

tggccgcaaa ttgcacaatt tgcccccagc gcttcagcgt tcttcggaat gtcgcgcatt    960

ggcatggaag tcacaccttc gggaacgtgg ttgacctaca caggtgccat caaattggat   1020
```

-continued

```
gacaaagatc caaatttcaa agatcaagtc attttgctga ataagcatat tgacgcatac   1080

aaaacattcc caccaacaga gcctaaaaag gacaaaaaga agaaggctga tgaaactcaa   1140

gccttaccgc agagacagaa gaaacagcaa actgtgactc ttcttcctgc tgcagatttg   1200

gatgatttct ccaaacaatt gcaacaatcc atgagcagtg ctgactcaac tcaggcctaa   1260


<210> SEQ ID NO 24
<211> LENGTH: 38
<212> TYPE: PRT
<213> ORGANISM: SARS CoV 2

<400> SEQUENCE: 24

Met Gly Tyr Ile Asn Val Phe Ala Phe Pro Phe Thr Ile Tyr Ser Leu
1               5                   10                  15

Leu Leu Cys Arg Met Asn Ser Arg Asn Tyr Ile Ala Gln Val Asp Val
            20                  25                  30

Val Asn Phe Asn Leu Thr
        35


<210> SEQ ID NO 25
<211> LENGTH: 116
<212> TYPE: RNA
<213> ORGANISM: SARS CoV 2
<300> PUBLICATION INFORMATION:
<301> AUTHORS: Wu,F., Zhao,S., Yu,B., Chen,Y.M., Wang,W., Song,Z.G.,
      Hu,Y.,Tao,Z.W., Tian,J.H., Pei,Y.Y., Yuan,M.L., Zhang,Y.L.,
      Dai,F.H.,Liu,Y., Wang,Q.M., Zheng,J.J., Xu,L., Holmes,E.C. and
      Zhang,Y.Z
<302> TITLE: A new coronavirus associated with human respiratory disease
      in China
<303> JOURNAL: Nature
<304> VOLUME: 579
<305> ISSUE: 7798
<306> PAGES: 265-269
<307> DATE: 2020-03-03
<308> DATABASE ACCESSION NUMBER: NC_045512
<309> DATABASE ENTRY DATE: 2020-07-08
<313> RELEVANT RESIDUES IN SEQ ID NO: (29558)..(29674)

<400> SEQUENCE: 25

atgggctata taaacgtttt cgcttttccg tttacgatat atagtctact cttgtgcaga     60

atgaattctc gtaactacat agcacaagta gatgtagtta actttaatct cacata        116
```

VIRAL PREPARATIONS AND METHODS FOR TREATING AND MODULATING MITOCHONDRIAL EFFECTS OF CORONAVIRUS INFECTIONS

CROSS REFERENCE TO RELATED APPLICATIONS

This application claims priority from U.S. Patent Provisional Application No. 63/049,125 filed Jul. 8, 2020.

REFERENCE TO SEQUENCE LISTING

The sequence listing for this application concurrently submitted under 37 C.F.R. 1.821 in Computer Readable Form in CD format via mail in two duplicated and identical CDs as a file named SeqList17368994.txt. The electronic copy of the Sequence Listing was created on Oct. 10, 2021 with a file size of 8.8 kilobytes.

BACKGROUND OF THE INVENTION

Field of the Invention

The present disclosure generally relates with engineered attenuate coronavirus species that are able to fully replicate and spread together with the methods of obtaining thereof. The engineered coronavirus species are intended to treat and prevent viral infectious disease including all those caused by coronavirus species that affect humans as the COVID-19 caused by the SARS-CoV2.

Description of the Background of the Invention

Coronaviruses (CoVs) are a group of related viruses that cause diseases in mammals and birds. In humans, coronaviruses cause respiratory tract infections that can range from mild to lethal. Mild illnesses include some cases of the common cold (which is caused also by certain other viruses, predominantly rhinoviruses), while more lethal varieties can cause severe acute respiratory syndrome (SARS), Middle East respiratory syndrome (MERS), and coronavirus disease 2019 (COVID-19). Symptoms in other species vary: in chickens, they cause an upper respiratory tract disease, while in cows and pigs they cause diarrhea. The human coronaviruses HCoV-OC43, HCoV-HKU1, HCoV-229E, and HCoV-NL63 continually circulate in the human population and produce the generally mild symptoms of the common cold in adults and children worldwide. Other human coronaviruses that showed to be lethal have been identified, including SARS-CoV in 2003, MERS-CoV in 2012, and SARS-CoV2 in 2019. A significantly larger number of animal coronaviruses were identified since the 1960s. During the last year some mRNA and viral vector vaccines to prevent SARS-CoV2 were approved and became available at some parts of the world, however production and distribution constraints that make them unavailable in many developing countries. At the moment of the priority provisional patent application of this invention were yet no vaccines or antiviral drugs available to prevent or treat human coronavirus infections.

Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface, which in electron micrographs create an image reminiscent of the solar corona, from which their name derives. Coronaviridae genomes comprise a G and C base contents varying from 32% to 43%. Variable numbers of small open reading frames (ORFs) are present between the various conserved genes (ORF1a/b, spike or S, envelope or E, membrane or M and nucleocapsid or N) and, downstream to the nucleocapsid gene in different coronavirus lineages. Subdivisions of ORFs in a and b correspond to different starting reading codons, usually atg, at the same gene. The viral genome contains distinctive features, including a unique N-terminal fragment within the spike protein. Genes for the major structural proteins in all coronaviruses occur in the 5'-3' order as S, E, M, and N. A typical CoV contains at least six ORFs in its genome. The first ORF (ORF1a/b), about two thirds of the whole genome length, encode 16 non structural proteins (nsp1-16) excepting for Gammacoronavirus that lakes nsp1. ORF1a and ORF1b contain a frameshift in between which produces two polypeptides: pp1a and pp1ab. These polypeptides are processed by virally encoded chymotrypsin-like protease (3CL-pro) or main protease (Mpro) and one or two papain-like protease into 16 nsps. All the structural and accessory proteins are translated from the sgRNAs of CoVs. Four main structural proteins contain spike(S), membrane (M), envelope (E), and nucleocapsid (N) proteins are encoded by ORFs 10, 11 on the one-third of the genome near the 3'-terminus. Besides these four main structural proteins, different CoVs encode special structural and accessory proteins, such as hemagglutinin esterase (HE) protein, 3a/b protein, and 4a/b protein. These mature proteins are responsible for functions believed to be related to genome maintenance, host interaction and virus replication. The SARS, MERS, and COVID-19 epidemics brought new attention to coronavirae genomes and as consequence SARS-CoV, MERS-CoV and SARS-CoV2 proteomes became well characterized. They encode by a relatively similar set of ORFs between the S gene, the E, M, and N genes. The proteome of these ORFs are the corresponding OFRs 3 (subdivided in 3a and 3b in SARS-CoV), 6, 7 (equivalent to 4 and 5 respectively in MERS-CoV), 8 (subdivided in 8a and 8b in SARS-CoV and not present in MERS-CoV) and 10 (only present in SARS-CoV2). Current understanding indicates that these OFRs play no significant role in virus replication, but showed to have pathological roles in host interaction. Notably the SARS-CoV and SARS-CoV2 have an additional OFR at the N gene, the OFR 9b. There is a nonhomologous equivalent in MERS-CoV, the OFR 8b. When translated the OFR 9b is an 98 residues protein from SARS-CoV and an 97 residues protein from SARS-CoV2, sharing 84% of positives, 72% of identities and one gap. OFR 9b has no other known homologue in non CoV viruses. A resolved crystal structure revealed a dimeric tentlike β structure with an amphipathic surface and a central hydrophobic cavity that most likely mediates membrane attachment.

COVID-19 symptoms, caused by SARS-CoV2, include fever, cough, fatigue, shortness of breath, and loss of smell and taste. While the majority of cases result in mild symptoms, some progress to acute respiratory distress syndrome (ARDS) likely precipitated by a cytokine storm, multi organ failure, septic shock, and blood clots. The virus is primarily spread between people during close contact, most often via small droplets produced by coughing, sneezing, and talking. The droplets usually fall to the ground or onto surfaces rather than traveling through air over long distances. Less commonly, people may become infected by touching a contaminated surface and then touching their face. It is most contagious during the first three days after the onset of symptoms, although spread is possible before symptoms appear, and from people who do not show symptoms. The standard method of diagnosis is by real-time reverse transcription polymerase chain reaction (rRT-PCR) from a nasopharyngeal swab. First registered case of COVID-19 occurred at November 17 of 2019, in a June 2020 more than 6 million of cases have been reported in 188 countries and territories, resulting in more than 400000 deaths[1] and by June 2021 180 million of cases and 3.9 million of deaths were registered. Many of the details of COVID-19 are still under investigation. It spreads easily between people—easier than influenza but not as easily as measles. Estimates of the number of people infected by one person with COVID-19 (the R0) have varied widely. The WHO's initial estimates of the R0 were 1.4-2.5 (average 1.95), however a more recent review found the basic R0 (without control measures) to be higher at 3.28 and the median R0 to be 2.79. Notably the time from exposure to onset of symptoms is typically around five days but may range from two to fourteen days with approximately 10% of cases exceeding that time.

SARS is a viral respiratory disease of zoonotic origin that surfaced in the early 2000s caused by SARS-CoV, the first-identified strain of the SARS coronavirus species severe acute respiratory syndrome-related coronavirus (SARSr-CoV). The syndrome caused the 2002-2004 SARS outbreak. In late 2017, Chinese scientists traced the virus through the intermediary of Asian palm civets to cave-dwelling horseshoe bats in Yunnan province. SARS was a relatively rare disease; at the end of the epidemic in June 2003, the incidence was 8,422 cases with a case fatality rate (CFR) of 11%. No cases of SARS-CoV have been reported worldwide since 2004

MERS, also known as camel flu, is a viral respiratory infection caused by the MERS-CoV. Symptoms may range from none, to mild, to severe. Typical symptoms include fever, cough, diarrhea, and shortness of breath. The disease is typically more severe in those with other health problems. MERS-CoV is a coronavirus believed to be originally from bats. However, humans are typically infected from camels, either during direct contact or indirectly. Spread between humans typically requires close contact with an infected person. Its spread is uncommon outside of hospitals. Thus, its risk to the global population is currently deemed to be fairly low. Diagnosis is by rRT-PCR testing of blood and respiratory samples. The World Health Organization (WHO) recommends that those who come in contact with camels wash their hands and not touch sick camels. They also recommend that camel-based food products be appropriately cooked. Treatments that help with the symptoms and support body functioning may be used. The first identified case occurred in 2012 in Saudi Arabia and most cases have occurred in the Arabian Peninsula. About 2,500 cases have been reported as of January 2020. About 35% of those who are diagnosed with the disease die from it. Larger outbreaks have occurred in South Korea in 2015 and in Saudi Arabia in 2018.

SARS-CoV and SARS-CoV2 infected cells have an impaired IFN response, suggesting that the virus disrupts the normal host cell IFN response. How coronaviruses subverts the host IFN response is poorly understood. Yet, IFN therapy has also been suggested to be efficacious for SARS-CoV and SARS-CoV2 patients. The activation of the type 1 IFN pathway is crucial for the control of many viral infections. Following viral invasion, host cells detect the presence of viral RNA by endosomally localized TLR and cytosolic sensors of the retinoic-inducible gene-I (RIG-I)-like receptor (RLR) pathway, RIG-I and melanoma differentiation-associated gene 5 (MDA5). To better understand intracellular immune response it is necessary to understand the role of mitochondria. The mitochondrion, plural mitochondria, is a semi autonomous double-membrane-bound organelle found in most eukaryotic organisms. The most prominent roles of mitochondria are to produce the energy currency of the cell, ATP (i.e., phosphorylation of ADP), through respiration, and to regulate cellular metabolism. Besides their recognized role in energy production, mitochondria serve as a platform for host defense against RNA viruses such as coronaviruses. Although the above RIG-I and MDA5 differ in the types of viral RNA that they recognize, they share a common signaling path way that utilizes the adaptor protein, mitochondrial antiviral signaling protein MAVS (also known as ISP-1/VISA/Cardiff). MAVS recruits the E3 ligases TRAF3 and TRAF6, facilitating the activation of IFN regulatory factors (IRFs), NF-kB, and the induction of a host antiviral state. Many RNA viruses have evolved strategies to antagonize the type I IFN signaling pathways. MAVS and MAVS signaling are common targets. Mitochondrial-localized MAVS links mitochondria to antiviral type I IFN signaling.

During the first three months of the COVID-19 pandemic was notably observed a fast grow of infection in certain European and Asian countries whereas in others the infection rate was significantly slow even if those different countries are adjacent with a fluent traffic of people. Furthermore these initial contagious rates later correlated with mortality rates, specially in western European countries were some mitochondrial haplogroups has higher prevalence. These fast infection rate grow-high mortality countries correlates with a higher prevalence of the mitochondrial haplogroups as H and lower prevalence of haplogroups as U[3,4] suggesting that SARS-CoV2 may have some effect on the mitochondria of infected cells. Some OFR were found in mitochondria of SARS-CoV cells[5,6], notably it was shown that OFR-9b localizes to the outer mitochondria membrane of infected cells and that probably as a consequence, mitochondria elongate and mitochondrial antiviral signaling is disturbed. Mitochondrial fusion and fission maintain mitochondrial number, morphology, and function. In the initial step of fission, the dynamin-related protein DRP1 is recruited to mitochondria, where it assembles into a fission complex. Mitochondrial elongation is most likely caused by triggering DRP1 ubiquitination and its proteasomal destruction. ORF-9b also limits host cell IFN signaling and coimmunoprecipitates with the mitochondrial adaptor protein MAVS. ORF-9b-mediated reduction in DRP1 may also contribute to the decrease in type I IFN signaling; however, other mechanisms must be operant. It is hypothesized that ORF-9b counteracts the impact of other cellular stresses during SARS-CoV and SARS-CoV2 infections, which fragment and aggregate mitochondria, thereby helping to promote cell survival during viral replication. Mitochondrial fusion is known to protect mitochondria from starvation-induced autophagosomal degradation often common in viral infections. In fact ORF-9b most likely has little role in directly supporting viral replication, but rather its primary function is to inactivate the RLR pathway by triggering degradation of the MAVS/TRAF3/TFAF6 signalosome. ORF-9b may counteract the impact of other cellular stresses during SARS-CoV and SARS-CoV2 infections, which fragment and aggregate mitochondria, thereby helping to promote cell survival during viral replication.

Mitochondrial fusion is known to protect mitochondria from starvation-induced autophagosomal degradation and explain the long incubation times with latent symptoms observed in SARS-CoV2 infections therefore neutralizing this mechanism is a eventual treatment for COVID-19 and other CoV diseases.

Published studies[6,19] show that past infection provides effective and probable long-term immunity in people who recover from most acute respiratory CoV caused (SARSn-CoV) diseases. Some of the infected have been reported to develop protective antibodies, so acquired immunity is presumed likely, based on the behavior of other coronaviruses. Cases in which recovery from COVID-19 was followed by positive tests for coronavirus at a later date have been reported. However, these cases are believed to be lingering infection rather than reinfection, or false positives due to remaining RNA fragments. Investigations in subjects who tested positive for SARS-CoV2 in PCR tests administered days or weeks after recovery from COVID-19 found no evidence that these subjects were contagious at this later time. Some other coronaviruses circulating in people are capable of reinfection after roughly a year.

As today there are around ten vaccines clinically in use to prevent SARS-CoV2 and various agencies are actively developing additional ones. Previous work on SARS-CoV was extensively used because both SARS-CoV and SARS-CoV2 use the angiotensin converting enzyme-2 (ACE2) receptor to enter human cells. All them are based on three vaccination strategies. First, the use of a whole virus, inactive or dead, to elicit a prompt immune response of the human body to a new infection with COVID-19. These are called inactivated vaccines, vaccines consisting of virus particles that have been grown in culture and then lose replicate and disease producing capacity. A second strategy, subunit vaccines, aims to create a vaccine that sensitises the immune system to certain subunits of the virus. In the case of SARS-CoV2, such research focuses on the S-spike protein that helps the virus intrude the ACE2 enzyme receptor. A third strategy is that of the nucleic acid vaccines (DNA or RNA vaccines, a novel technique for creating a vaccination) to produce certain subunits of the virus, mostly at the N and S genes.

Antibody-dependent enhancement (ADE) has been suggested as a potential challenge for vaccine development for SARS-CoV2 and eventually for other coronaviruses. ADE, sometimes less precisely called immune enhancement or disease enhancement, is a phenomenon in which binding of a virus to non-neutralizing antibodies enhances its entry into host cells, and sometimes also its replication. This phenomenon—which leads to increased of infectivity and virulence—has been observed in coronaviruses.

New medications may take after 2021 to develop and temporally several of the medications being tested are already approved for other uses or are already in advanced testing stages. Antiviral medication may be tried in people with severe disease. The FDA has granted temporary authorization to convalescent plasma as an experimental treatment in cases where the person's life is seriously or immediately threatened, however the clinical studies needed to show it is safe and effective for the disease has not undergone and convalescent plasma is cumbersome and therefore not suitable for massive administration.

Reverse genetics made possible to construct complementary DNA (cDNA) templates from single-stranded RNAs of many coronaviruses that can be edited and translated again into RNA or prepare cDNA plasmids to be injected in cells. This gene edition involves epidemiological risks and can even evolves in biological warfare. In addition the genetic structure of many similar coronaviruses makes possible their recombination in vivo or in vitro by selecting preferred different CoV strains, infecting cells with a combination of viruses, genes and/or ORFs of these CoVs and recombining them in new CoV species without the need more complex techniques as gene edition. The former was observed in bats[20] and the later was performed experimentally in laboratories[21]. It was speculated that SARS-CoV2 is a recombination of different CoVs that infect different host spices. As today there is no direct evidence of SARS-CoV2 engineered recombination and there are natural recombination processes that can explain SARS-CoV2 emerging, however engineered recombination is not discarded and having formulations and methods to defeat emerging engineered viruses are actually a real need. Classically, reverse genetic systems for coronaviruses have been complicated by their large genome size (~30,000 nucleotides) and the existence of bacteriotoxic elements in their genome that make them difficult to propagate. Several approaches have been devised to overcome this barrier, such as multiple plasmid systems to disrupt toxic elements and to reduce deletions and mutations. Applying this approach, researchers have developed infectious clones for several coronaviruses, including SARS-CoV, MERS-CoV, SARS-CoV2, and other CoVs. Furthermore attenuated CoVs were proposed in the past as vaccines for animals[2], but never targeting proteins or genes that affect mitochondrial function in hosts. In fact the genes removed or silenced in these works have no homologous equivalent in SARSn-CoVs despite they may have similar names due to their position at the viral genome.

Mass production of vaccines and treatment is most likely limited by production, licensing costs and other constraints. As today there are hundred of vaccines and treatments on development it is estimated and around 10 effective vaccines are already available. Their equitable access among developed and undeveloped countries or regions showed to be compromised. WHO, other non profit private organizations and mixed consortia are committing money and organizational resources for the prospect that several vaccines will be 30 needed to prevent continuing COVID-19 infection. Support from these bodies maybe conditioned by internal and/or external political or corporate interests however. In addition the vaccines require custom formulation, special packaging, transportation, and storage in all 200 countries with infected citizens. Neither of the current vaccine and treatments approaches include an attenuate virus able to fully replicate and spread. Such attenuated CoV should be obtained with current laboratory methods and if it is proven to be safe, its the availability will not require significant distribution and production resources as common drugs does.

SUMMARY OF THE INVENTION

It is an objective of the invention to provide attenuated engineered mild symptomatic versions of otherwise harmful coronaviruses.

It is further an objective of the invention to provide a treatment for harmful coronaviruses based in attenuated engineered versions of the same.

It is also an objective of the invention to provide a vaccine for coronaviruses based in attenuated engineered versions of the same.

It is even an objective of the invention to provide an antidote for biological weapon based in an harmful engineered coronavirus by engineering an attenuated versions of the former.

It is also an objective of the invention to produce any of the attenuated viruses of above able to fully replicate and spread between living beings including humans.

For the purposes of this invention an accepted medical or veterinary formulation is any formulation or composition approved as safe and effective for therapeutic use in any territory by a valid regulatory agency as the Food and Drug Agency (FDA) in the United States. For other countries, regions and sovereignties other agencies may apply.

Also for the purposes of this invention gene editing is any type of genetic engineering in which DNA and/or RNA, including the corresponding cDNA, are inserted, deleted, modified or replaced in the genome of any organism.

These and other features, aspects, and advantages of the present invention will become better understood upon consideration of the following detailed description, drawings and appended claims.

BRIEF DESCRIPTION OF THE DRAWINGS

FIG. 3 is a schematic representation of the suppression of the protein translated by the OFR 9b gene of SARS-CoV, SEQ ID NO: 22.

FIG. 4 is a schematic representation of the suppression of the protein translated by the OFR 9b gene of SARS-CoV2, SEQ ID NO: 23 and, SEQ ID NO: 2.

FIG. 6 is a schematic algorithm for the obtaining of an attenuated CoV from other infecting CoV.

FIG. 7 is a schematic algorithm for the obtaining of a vaccine or a treatment for a CoV disease.

FIG. 8 is a schematic algorithm for the obtaining of an antidote for a CoV based weapon.

FIG. 9 is a schematic representation of maps showing the geographical distribution of some mitochondrial haplogroups in Europe, part of Africa and part of Asia.

Like reference numerals will be used to refer to like parts from Figure to Figure in the following description of the drawings.

DETAILED DESCRIPTION OF THE INVENTION

Figure 1:
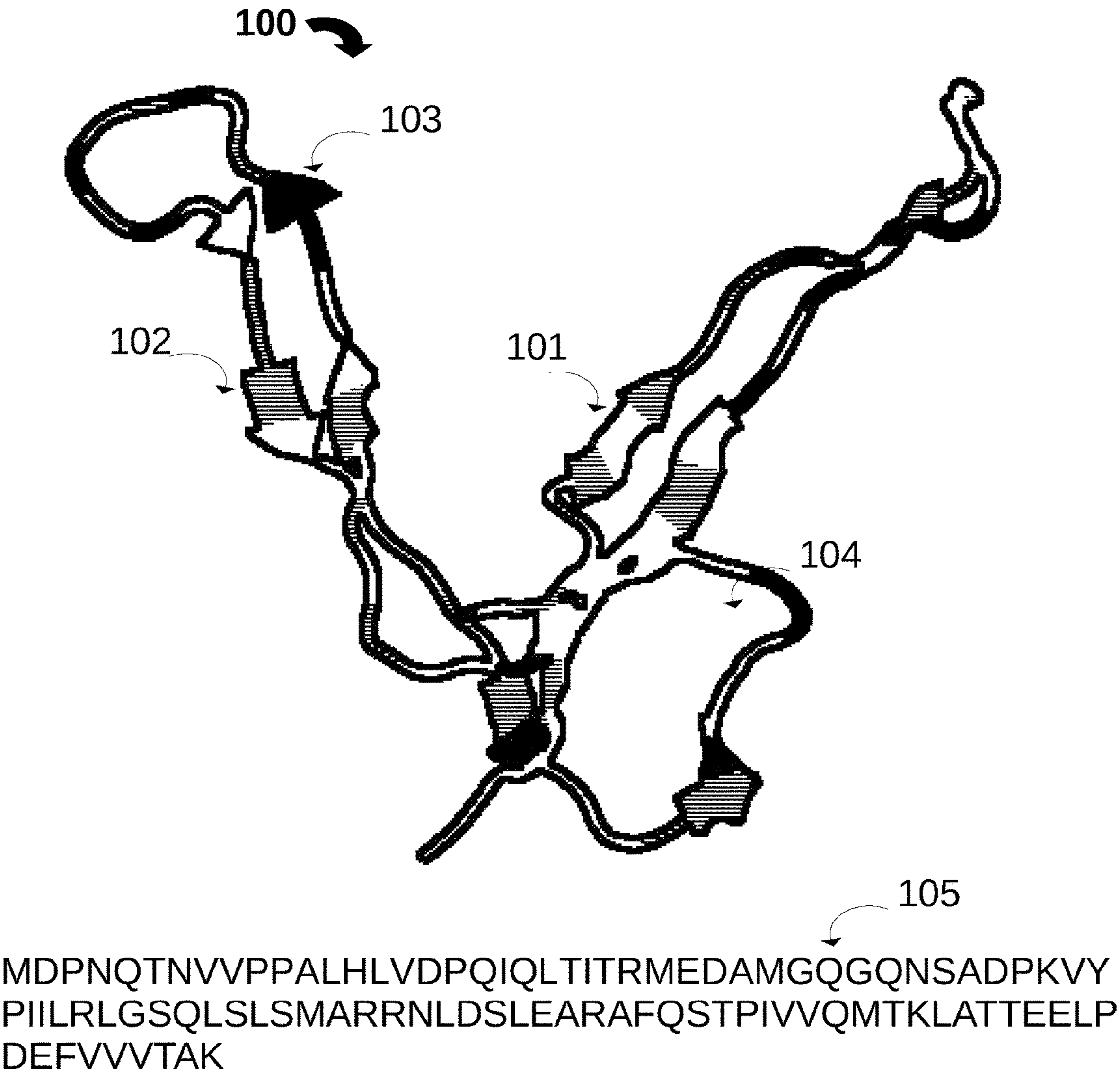
FIG. 1 is a schematic representation of the protein translated by the OFR 9b gene of SARS-CoV, SEQ ID NO: 20.

For obtaining the above attenuated viruses some of the embodiments of the invention generally can involve a six steps procedure 1. Detecting at least one protein that affect mitochondrial function
2. Identifying in a virus the genes that produce these at least one protein
3. Creating a viral infecting clone of the virus
4. Deleting and/or silencing the genes of step 2
5. Replicating the clone
6. Infecting cell, animals and/or human subjects to test the safety, effectiveness and infecting rate of the infecting clone virus.

Steps 2 and/or 3 can be replaced by any other gene editing technique that may reduce or increase the total number of the steps of the procedure.

One of the mechanism in which SARS-CoVs affect mitochondria may involve the release of proteins that interfere with mitochondrial function, as for example the one translated by the OFR 9b gene described in previous sections and its homologous. By affecting the mitochondrial immune function, virions can produce and replicate into the infected cells for longer times diminishing extracellular immune response and increasing viral production. In order to provide to host an immune response to those SARSn-CoVs, in some of the embodiments of the invention is obtained an infectious clone (ic) of CoVs in which the transcription of any protein that affect mitochondrial function is deactivated and or removed without affecting the viral capabilities to infect and replicate. Homologous to the OFR 9b protein in different CoVs can be translated by alternative OFRs as 10, 11, 13 or 14 depending on the specific CoV. These homologous are often slightly less than 100 amino acid viral accessory proteins encoded from a complete internal ORF within the N gene of bicistronic nature. In SARS-CoV2 some researches refer to the OFR 9b protein as OFR 9a or 14[22]. There are other SARSn-CoV proteins that are or were believed to affect mitochondrial function. These include OFRs 8a and 3b in SARS-CoV and 8, 10 in SARS-CoV2, however a 382 nucleotide deletion covering almost the entire ORF8 of SARS-CoV was observed in eight hospitalized patients in Singapore[23] without a significant pathological difference compared to the cases where the OFR 8 is present. Remarkably, another genotype with a 415-nt deletion resulting in the loss of the whole ORF 8 region was isolated and confirmed in two Hong Kong patients with disease onset from mid-May 2003. Furthermore a natural occurring variation at the 29-tn that binds OFRs 8a and 8b in a single larger gene was also observed in some patients[24] without clinical effects. This indicates that the removal of OFR 8 alone is probably not effective as treatment. OFRs 3b and 8a from SARS-CoV were also found in mitochondria, however they are believe to induce cell apoptosis and therefore shortening cell life and viral production cycle, it is unclear any effect on mitochondrial function and their overall pathological effect is still unknown. By the other hand OFR 10 protein of SARS-CoV2 is also indicated to affect mitochondrial function. From computerized modeling secondary structure of OFR 10 seems to be composed by a pair of mostly polar anti parallel beta sheets and a third one in a perpendicular loop having three anchoring segments that predict a transmembrane domain that allows OFR 10 protein to bind and precipitate other proteins and to interact with intracellular membranes.

One strategy to obtain an attenuated CoV with a minimized effect on mitochondrial is to remove or silence any gene with proven effect on mitochondrial function as can be OFR 9b or OFR 10 as are detailed in the examples bellow.

Preparation of CoVs with Attenuated Effect on Mitochondrial Function

Infectious OFR 9b or OFR 10 Free Mutant SARS-CoV-2

SARS CoV 2 or infectious clone (ic) recombinant virus ic strains of SARS-CoV 2(NC_045512) are propagated on Vero E6 cells in Eagle's minimal essential medium supplemented with 10% fetal calf serum, kanamycin (0.25 μg/ml), and gentamicin (0.05 μg/ml) at 37° C. in a humidified CO2 incubator. For virus growth, cultures of Vero E6 cells are infected at a multiplicity of infection (MOI) of 5 for 1 h and the monolayer washed two times with 2 ml of phosphate-buffered saline (PBS) and overlaid with complete minimal essential medium. Virus samples are then harvested at different times postinfection and titered by plaque assay in 60 mm2 dishes. Plaques are visualized by neutral red staining and counted at 48 h. All virus work shall be performed in a biological safety cabinet in a biosafety level 3 (BSL3) laboratory containing redundant exhaust fans. Personnel shall to be double-gloved and dressed in appropriate suits with full hoods and face shields. Powered air-purifying respirators with high-efficiency particulate air and organic vapor filters shall to be used to provide a positive-pressure environment within the hoods.

Viral RNA, extracted from the passage 4 SARS-CoV2 virus from Vero E6 cells, is used as a template for RT-PCR to produce cDNA fragments. Seven contiguous cDNA fragments F1 to F7 are constructed to cover the entire viral genome taking two different approaches. Some of the seven cDNA fragments are prepared through RT-PCR, whereas others are generated by chemical synthesis. First, the cDNAs of fragments F1, F4, F5, and F6 are synthesized from the GenScript company (Piscataway, NJ) and cloned into a high-copy plasmid pUC57. The F1 contains a T7 promoter sequence at the upstream of the 5' end of the SARS-CoV2 sequence. The cDNAs of fragments F2, F3, and F7 are obtained by reverse transcription and PCR (RT-PCR). RT is performed by using the SuperScript IV First-Strand Synthesis System (ThermoFisher Scientific) with random hexamer primers and extracellular viral RNA (extracted from the supernatants of SARS-CoV2 infected Vero E6 cells). The cDNA is used as a template to amplify the fragments F2, F3, and F7 by high fidelity PCR with the Platinum SuperFi II DNA Polymerase (ThermoFisher Scientific). A poly (T) 29 sequence is introduced by PCR to the 3' end of the untranslated region of viral genome. The amplicons are cloned into a single-copy vector pCC1BAC (Epicenter) to increase the stability of the cDNA plasmids when propagated in *E. coli*. To ensure a seamless assembly of the full-length cDNA, two cleavage sites of class IIS restriction enzymes (BsaI and Esp3I) are introduced at both ends of each sibling cDNA during PCR or gene synthesis. To differentiate the infectious clone-derived virus from the parental isolate silent mutations can be engineered at for example nucleotide positions 7,486 (A-to-T change), 7,489 (T-to-A change), and 18,058 (T-to-C change) corresponding to NC_045512 or their equivalent located using the BLAST database alternatively can be used other comparative method to differentiate mutants.

The suppression of ORF9b in the N gene coding region at F7 is achieved by mutating the initiation codon of ORF9b at F7 from ATG to ACG, located at position 28284 in ascension NC_045512.

The suppression of ORF10 in the coding region at F7 is achieved by mutating the initiation codon of ORF10 at F7 from ATG to ACG, located at position 29558 in ascension NC_045512. It may be also possible to delete the complete ORF 10, however is still unclear if the ORF 10 is totally or partially part of a bigger bicistronic ORF structure.

If desired deletion of OFR 8 gene can be introduced by overlap extension PCR in the F7 plasmid template. Mutated plasmids can be confirmed by sequence analysis.

To assemble the full-length cDNA, subject cDNA plasmids are digested and purified each cDNA fragment. Specifically, F1, F2, F3 and F4 cDNA fragments are obtained by digesting the corresponding plasmids with enzyme BsaI. F5 and F6 fragments are obtained by digesting the plasmids with enzymes Esp3I and PvuI. F7 and F7-mNG cDNA fragments are obtained by digesting the corresponding plasmids by Esp3I and SnaBI. PvuI and SnaBI are included in the digestion to eliminate undesired DNA bands that co-migrated with the targeted fragments on agarose gels. All fragments after restriction enzyme digestion are separated on 0.6% agarose gels, visualized under a darkreader lightbox (Clare Chemical Research, Dolores, CO), excised, and purified using the QIAquick Gel Extraction Kit (QIAGEN, Germantown, MD). To assemble the full-length cDNA, the seven cDNA fragments are ligated in a three-step manner. First, equimolar amounts of F1 (0.61 μg), F2 (0.65 μg), F3 (0.75 μg), and F4 (0.94 μg) are ligated in a PCR tube using T4 DNA ligase in a 40 μl-reaction at 4° C. for 18 h, resulting in F1-4 DNA. Second, equimolar amounts of fragments F5 (0.75 μg), F6 (0.72 μg), and F7 (0.60 μg) are ligated in a separate PCR tube to produce F5-7 DNA using the same ligation conditions. Third, without any DNA purification, the two reactions (containing F1-4 and F5-7) are combined (total 80 μl) and topped with additional T4 ligase (2 μl), buffer (2 μl) and nuclease-free water (16 μl) to a 100 μL reaction. The final reaction is incubated at 4° C. for 18 h to produce the full-length F1-7 DNA. Afterward, the full-length cDNA is phenol/chloroform extracted, isopropanol precipitated, and resuspended in 10 μL nuclease-free water.

To recover recombinant SARS-CoV2 from the infectious cDNA clone (icSARS-CoV2), the in-vitro-transcribed genome-length RNA is electroporated into Vero E6 cells. RNA transcript can be in vitro synthesized by electroporating the RNA transcription mixture into cells without purification for using for example the mMESSAGE mMACHINE T7 Transcription Kit (ThermoFisher Scientific). A 50 μL reaction is set up by adding 1 μg DNA template and 7.5 μL GTP (cap analog-to-GTP ratio of 1:1). The reaction is incubated at 32° C. for 5 h. After removing the template DNA by nuclease per manufacturer's protocol, the RNA is phenol/chloroform extracted and isopropanol precipitated. Given that N protein was reported to enhance the infectivity of coronavirus RNA transcripts [Curtis et al., 2002; Yount et al., 2003; Yount et al., 2002], an mRNA is co-electroporated encoding the SARS-CoV-2 N protein with the full-length RNA. A SARS-CoV2 N gene transcript is in vitro transcribed from a DNA template using the mMESSAGE mMACHINE T7 Transcription Kit with a 2:1 ratio of cap analog to GTP. The N gene DNA template is prepared by PCR using primer Cov-T7-N-F (tactgTAATACGACTCACTATAG-Gatgtctgataatggaccccaaaatc; the uppercase sequence represents T7 promoter; the underlined sequence represents the 5' end of N gene. ęSEQ ID NO: 4) and primer polyT-N-R [$(t)_{37}$aggcctgagttgagtcagcac. SEQ ID NO: 5]. In order to delete the ORF 9b the initiation codon of ORF 9b at gene N is mutated from ATG to ACG, located at position 10 of the gene, however this step is not necessary if ORF 9b deletion is not pursued. Mutated plasmids can be confirmed by sequence analysis. RNA transcripts are electroporated into Vero E6 cells. Twenty micrograms of total RNA transcripts (containing both full-length RNA and short RNAs) and 20 μg N gene transcript are mixed and added to a 4-mm cuvette containing 0.8 mL of Vero E6 cells ($8\times10^6$) in Ingenio® Electroporation Solution (Mirus). Single electrical pulse was given with a GenePulser apparatus (Bio-Rad) with setting of 270V at 950 μF. After 5 min recovery at room temperature, the electroporated cells are seeded into a T-75 flask and incubated at 37° C. with 5% $CO_2$. On the next day, the culture fluid is replaced with 2% FBS DMEM medium. The cells are monitored daily for virus-mediated cytopathic effect (CPE). One milliliter of the P0 virus is inoculated to a T-175 flask containing 80% confluence Vero E6 cells. The infected cells are incubated at 37° C. with 5% $CO_2$ for 2-3 days. Culture supernatants (P1) are harvested when CPE occurred. The amount of infectious virus is determined by a standard plaque assay on Vero E6 cells. All virus cultures shall to be performed in a biosafety level 3 (BSL-3) laboratory with redundant fans in the biosafety cabinets. Personnel shall to wear powered air purifying respirators with appropriate suits, aprons, booties, and double gloves.

Infectious OFR 9b Free Mutant SARS-CoV

Strains of SARS-CoV are propagated in VeroE6 cells in MEM supplemented with 10% FCS, kanamycin (0.25 μg/ml), and gentamycin (0.05 μg/ml) at 37° C. in a $CO_2$ incubator. Cultures of VeroE6 cells are infected at a multiplicity of infection of 0.1 for 30 min, washed, and titered by plaque assay. At 1 h after infection, some cultures are treated with the cysteine protease inhibitor (2S,3S)-transepoxysuccinyl-L-leucylamido-3-methylbutane ethyl ester (E64-d) at a concentration of 500 μg/ml. Virus plaques are visualized by neutral red staining at 2 d after infection. Reverse transcription is performed by using SuperScript II, oligodeoxynucleotide primers, and intracellular RNA from SARS-infected cultures. The cDNA is denatured for 2 min at 94° C. and amplified by PCR with Expand Long TAQ polymerase (Roche Molecular Biochemicals) for 25 cycles at 94° C. for 30 sec, 58° C. for 25-30 sec, and 68° C. for 1-7 min. The amplicons are cloned into Topo II TA (Invitrogen) (SARS subclones D-F) or in pSMART vectors (Lucigen, Middleton, WI) (SARS subclones A-C). All cDNAs are assembled as CSs based on independent sequence analysis of four to seven sibling clones and the reported Urbani sequence. The following primers are used in the isolation of the SARS A subclone (forward, tactaatacgactcactatagatattaggtttttacctacccagg-1, SEQ ID NO: 6 Reverse, acaccatagtcaacgatgcc-4452, SEQ ID NO: 7); SARS B subclone (forward, gcctatatgcatggatgttagat-4359, SEQ ID NO: 8. Reverse, tgaaccgccacgctggctaaacc-8727, SEQ ID NO: 9); SARS C, subclone (forward, agccagcgtggcggttcatac-8710, SEQ ID NO: 10. Reverse, aggcctcttgggcagtggcataag-12085, SEQ ID NO: 11); SARS D subclone (forward, actgcccaagatgcctatgagc-12070, SEQ ID NO: 12. Reverse, cagccaggagggcagacttcacaacc-18939, SEQ ID NO: 13); SARS E subclone (forward, gtctgccctcctggctgataagtttccag-18923, SEQ ID NO: 14. Reverse, gagcagccgtgtaggcagcaat-24066, SEQ ID NO: 15); and SARS F subclone (forward, attgctgcctacacggctgctc-24045, SEQ ID NO: 16. Reverse, (ttt) 7 gtcattctcctaagaagc-29710, SEQ ID NO: 17).

To repair sibling clones, primer pairs are designed that contained a class IIS restriction enzyme, like AarI. By using high fidelity PCR, the consensus portions of different sibling clones are amplified, digested with AarI, and ligated into plasmid. The AarI junctions are designed to seamlessly link consensus fragments, resulting in the production of a full-length cDNA fragment for each of the various SARS cDNA subclones. By using an automated Applied Biosystems DNA sequencer, two to three candidate DNAs are sequenced to identify the consensus clone.

The SARS A-F inserts are restricted, separated through 0.8% agarose gels, visualized with a darkreader lightbox (Clare Chemical Research, Dolores, CO), excised, and purified by using the Qiaex II DNA purification kit. The SARS A+B, C+D, and E+F subclones are ligated overnight and isolated. The SARS AB+CD+EF cDNAs are ligated overnight at 4° C., phenol/chloroform extracted and precipitated. Transcripts are generated in vitro (TmMessage mMachine, Ambion) as described by the manufacturer with certain modifications. For SARS N transcripts, 1 μg of plasmid DNA encoding the N gene (primer: 5'-nnggcctcgatggccatttaggtgacactatagatgtctgataatgg-accccaatc-3', SEQ ID NO: 18, and reverse primer (5'-nnnttttttttttttttttttttttt-tatgcctgagttgaatcagcag-3', SEQ ID NO: 19) were transcribed by SP6 RNA polymerase with a 2:1 ratio of cap analog to GTP. The deletion of ORF9b in the N gene coding region at was achieved by mutating the initiation codon of ORF9b at F7 as well at the SARS N transcripts, from ATG to ACG, located at position 10 in the SARS N sequence, equivalent to the 28130 and 28277 positions at the Urbani and the obtained mutated infecting clone respectively. If desired, the deletion of OFRs 8a and/or 8b genes can be implemented by overlap extension PCR in the F7 plasmid template. Mutated plasmids can be confirmed by sequence analysis.

RNA transcripts are added to 800 μl of the BHK cell suspension (8.0×10 6), and three electrical pulses of 850 V at 25 μF are given with a Gene Pulser II electroporator (Bio-Rad). The BHK cells are seeded with $1.0\text{-}2.0\times10^6$ VeroE6 cells in a 75-cm 2 flask and incubated at 37° C. for 2 d. Virus progeny are then purified by plaque assay. For fluorescent Ab staining, cells are washed in PBS and incubated with goat serum for 20 min at room temperature. The cells are washed, incubated with a 1:200 dilution of MHV polyclonal antiserum that cross reacts with the SARS N protein, and then incubated in Alexa 488 diluted 1:400 for 30 min. The cells can be fixed in 10% neutral, phosphate-buffered formalin for 24 h, rinsed for 30 min, and visualized under a fluorescent microscope.

To detect marker mutations inserted in the infectious clone (ic)SARS-CoV, intracellular RNA is isolated from either WT or icSARS-CoV-infected cells at 24 h after infection. After RT-PCR, should be obtained a 1668-nt amplicon (nucleotide positions 1007-2675) spanning the BglI site at position 1557 that had been ablated in the icSARS-CoV component clones, but not WT SARS-CoV.

Other PCR products included a 799-nt amplicon spanning the SARS-CoV B/C junction (nucleotide positions 8381-9180), a 544-nt amplicon (nucleotide positions 11721-12265) spanning the SARS-CoV C/D junction, a 652-nt amplicon spanning the SARS-CoV D/E junction, and a 1594-nt amplicon (nucleotide positions 23665-25259) spanning the SARS-CoV E/F junction. The 1594-nt SARS E/F junction-containing amplicon was subcloned and sequenced. Alternatively to the Urbani sequence for obtaining an infectious clone, the TOR-1, 2 or any other SARS-CoV sequence can be used and adapted.

The above example strategies to obtain an attenuate CoV can be applied to several CoV including some SARSn-CoV and bat CoV species that are believed the larger animal reservoir able to infect humans and that were largely studied [20]. The in vivo validation of the virus attenuation depends on the viral load. The viral pathological effects on mitochondrial immune mechanism modulates how long cells will survive producing virions and/or viral particles and providing a high initial viral dose may hide this effect. The vaccine effect in living beings have to be validated for being included in an accepted medical or veterinary formulation by providing doses comparable to natural occurring viral infective exposure and by evaluating kinetic curves of immune response, symptoms and infectious propagation rate. Low doses, less than 200 plaque forming units (PFU), of the above attenuated SARS-CoV in hACE-2 Tg mice, cause faster indication of infection as weight loss and fever than wild type SARS-CoV, however the mortality of the former is lower than the later. The same results are expected for SARS-CoV2. It have to be noted that the attenuation of the viral effect on mitochondrial function may decrease viral replication and release during the cell cycle but will not necessarily increase cell survival, therefore in vitro studies may not be indicative of the vaccine or therapeutic effects of the attenuated CoVs. 100 pfu is the expected dosage for human beings that may vary according to clinical and preclinical studies as well as clinical practice. A dosage greater than 200 pfu is expected to produce symptomatic illness in humans and may be not suitable for therapeutic use against most CoVs. All these variations are contemplated in the scope of the invention.

There are also alternative genome engineering approaches to obtain attenuated CoVs. These include for example meganucleases, zinc finger nucleases (ZFNs), transcription-activator-like effector nucleases (TALENs) and the clustered regularly interspaced short palindromic repeats (CRISPR/Cas9) system. All them fall in the scope of the invention including the use of engineered nucleases and/or any future or existing method of gene editing. Furthermore in alternative embodiments of the invention the RNA editing can be achieved directly by CRISPR. In 2016, researchers demonstrated that CRISPR from an ordinary mouth bacterium could be used to edit RNA[26]. The researchers searched databases containing hundreds of millions of genetic sequences for those that resembled CRISPR genes. They considered the fusobacteria *Leptotrichia shahii*. It had a group of genes that resembled CRISPR genes, but with important differences. When the researchers equipped other bacteria with these genes, which they called C2c2, they found that the organisms gained a novel defense. Bacteria with C2c2 make molecules that can dismember RNA, destroying the virus. Tailoring these genes opened any RNA molecule to editing.

Some of the above strategies to obtain an attenuated CoV leaves intact the gene S responsible of allowing cell penetration, however the invention is not limited to leave unaltered any specific gene. Gene S highly mutate and it is almost unique between different CoV species. Unlike the ACE2 receptor produced by the S gene of SARS-CoV which is activated by the serine protease TMPRSS2 which is very specific and located in cells of the upper respiratory tract in humans, the homologous ACE2 receptor of SARS-CoV2 is activated by the enzyme furin in a similar process as occur in other viruses as HIV and also some other CoVs as fpr example the MERS-CoV. Examination of the protein sequence of the S glycoprotein of SARS-CoV-2 reveals the presence of a furin cleavage sequence (PRRARS|V). The CoV with the highest nucleotide sequence homology, isolated from a bat in Yunnan in 2013 (RaTG-13)[27], does not have the furin cleavage sequence. Because furin proteases are abundant in the respiratory tract, it is possible that SARS-CoV2 S glycoprotein is cleaved upon exit from epithelial cells and consequently can efficiently infect other cells. In contrast, the highly related bat CoV RaTG-13 lacks the furin cleavage site. The second most closely related to SARS-CoV2 nucleotide sequence homology comes from pangolin-CoV which was discovered during the first half of 2019[29]. In fact the only known and identical homologous to OFR 10 protein was found in pangolin-CoV. Current genetic data show that until now, none of the coronaviruses caused epidemics are derived from a previously used virus template neither is evidence of the direct use of cDNA. However the possibility of an engineered recombination in vivo and/or in vitro exists. It may be possible to culture CoV RaTG-13 with other full CoV and, for example adding plasmids containing the S gene of other CoVs as can be MERS-CoV and later on to infect animals with one or more of the resulting CoV spices. Other co infection strategies can involve infecting with CoV RaTG-13 pangolins already infected with pangolin-CoV. As today there is no empirical evidence that these strategies to produce any CoV that may affect humans were used and any of these hypotheses has to be experimentally validated.

Referring to FIG. 1. An schematic computer rendered representation of the OFR 9b translated protein from SARS-CoV denoted as 100 is showed. Residues are represented by different filling layouts indicated as 101 hydrophobic residues without filling, 102 polar residues filled with a pattern of lines, 103 arg, lys, asp, glu charged residues filled in solid black. A central hydrophobic cavity 104 can be visualized. The corresponding protein sequence is in FIG. 105. SEQ ID NO: 20.

Figure 2:
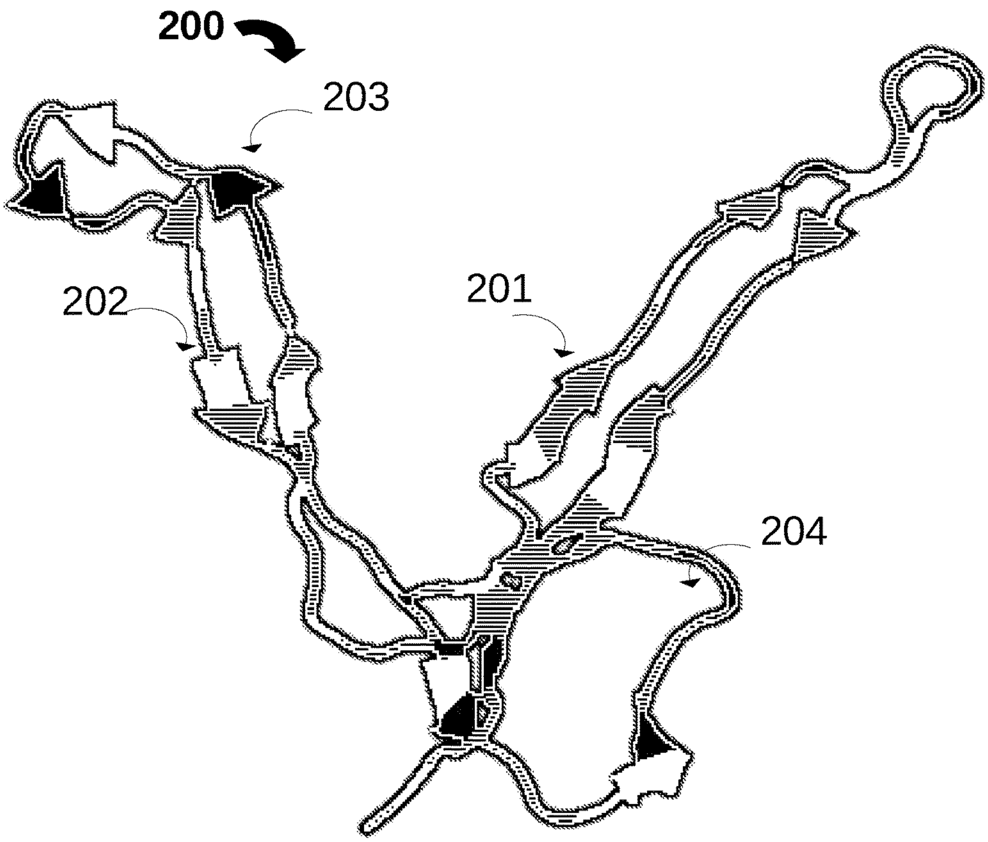
FIG. 2 is a schematic representation of the protein translated by the OFR 9b gene of SARS-CoV2, SEQ ID NO: 21.

Referring to FIG. 2. An schematic computer rendered representation of the OFR 9b, also referred as 9a by some researchers, translated protein from SARS-CoV2 denoted as 200 is showed. Residues are represented by different filling layouts indicated as 201 hydrophobic residues filled with a pattern of lines, 202 polar residues without filling, 203 arg, lys, asp, glu charged residues filled in solid black. A central hydrophobic cavity 204 can 21 be visualized. The corresponding protein sequence it is shown in 205. SEQ ID NO: 21.

Referring to FIG. 3. 300 shows the edition of the first codon from the OFR 9b SARS-CoV sequence ATG, 301, that is transformed into ATC, 302, at the $10^{th}$+2 position of the N gene as an example to suppress gene translation into protein. SEQ ID NO: 22 and SEQ ID NO: 1.

Referring to FIG. 4. 400 shows the edition of the first codon from the OFR 9b SARS-CoV2 sequence ATG, 401, that is transformed into ATC, 402, at the $10^{th}$+2 position of the N gene as an example to suppress gene translation into protein. SEQ ID NO: 23 and SEQ ID NO: 2.

Figure 5:
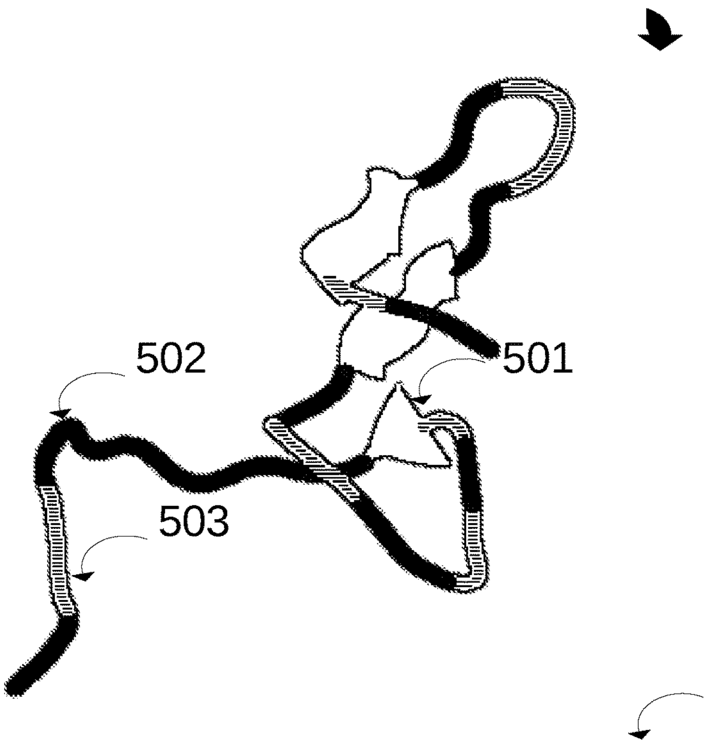
FIG. 5 is a schematic representation of the protein translated by the OFR 10 gene of SARS-CoV2 and its suppression, SEQ ID NO: 24 and, SEQ ID NO: 3.

Referring to FIG. 5. An schematic computer rendered representation of the OFR 10 translated protein from SARS-CoV2 denoted as **500*a* is showed. Residues are represented by different filling patterns indicated as 501 hydrophobic residues without filling, 502 polar residues filled in solid black, 503 arg, lys, asp, glu charged residues filled with a pattern of lines. The protein sequence is in 504, SEQ ID NO: 24. 500*b* shows the edition of the first codon from the OFR 10 sequence ATG, 505, SEQ ID NO: 25, that is transformed into ATC, 506**, SEQ ID NO: 3, as an example to suppress gene translation into protein.

Referring to FIG. 6. An simplified algorithm of an preferred method to obtain an attenuated coronavirus from a existing species is shown as a schematic flux diagram denoted as 600. An existing CoV is considered in box 610. The source of the CoV can be for example a biological sample originated from either an human or non human subject, cell cultures or it can be generated from an artificial or natural occurring genome. At step 620 a candidate protein is identified following different possible strategies that can include genome recognition, screening for known homologous proteins, intracellular characterization of cultures, molecular imaging, or even epidemiological correlation with mitochondrial haplogroups. In many published works, the effect in mitochondrial function was assessed by direct observation and localization at mitochondria after labeling the viral protein with a molecular imaging method as fluorescence, or by looking for labeling precipitates of proteins related to mitochondrial function [2]. Another possible approaches include changes in the characterization of mitochondrial DNA (mitDNA) for example using circular dichroism [25]. These techniques are only examples and there are many existing of future methods to assess the effect of viral composition on mitochondrial function and all of them fall into the scope of the invention. The result of this step leads to the obtaining of an attenuated CoV candidate if it is positive or, if it is negative, the method is discarded and the process finishes as shown in 630. Once at least one candidate gene and/or translated protein that affect mitochondrial function are identify, gene editing techniques are applied to remove any of them in step 640. These techniques can include the building of cDNA from RNA, full or partial genomes of infecting clones, the use of meganucleases, zinc finger nucleases (ZFNs), transcription-activator-like effector nucleases (TALENs) and the clustered regularly interspaced short palindromic repeats (CRISPR/Cas9) system or any existing or future gene editing technique. Once the new edited genome is obtained a new CoV is produced at 650 by a combination of for example reverse genetics, in vitro or in vivo injection of genetic material to bacteria or cells, in vitro or in vivo recombination of a combination of CoV strains, mRNA, cDNA plasmids or a combination thereof. The pathological effect of the newly obtained CoV candidate is addressed in 660 using any of the methods described in 620. If there no signification suppression of mitochondrial activity the candidate protein is discarded, step 695, and the process comes back to 620 for looking and alternative protein. In a further step it is evaluated by in vitro and in in vivo studies if the resulting CoV of step 650 can infect and replicate in cells. A preferred method to perform 670 is to collect the supernatant of infected cell cultures and look for released viral particles using a microscopy technique, but other existent and/or future method used in virology can be applied for this step. If proper infection and replication rates are measured then the desired attenuated new CoV was obtained, the algorithm moves to step 699 and finishes. Otherwise it should to be evaluated if the gene editing strategy was adequate. Step 680 considers if there exists an alternative gene strategy, if yes it is changed at step 690 and then step 650 and its subsequents are repeated. Otherwise there is no alternative gene editing technique to apply, the protein is discarded in step 695 and a new candidate protein have to be identified in step 620. There are a finite number of proteins and gene editing techniques to test and at the overall after a finite number of steps the algorithm have to give one result. A new CoV is obtained, box 699, or the method have to be discarded, box 630.

Referring to FIG. 7. An simplified algorithm of a preferred method to obtain a vaccine or treatment for an existing CoV is shown as a schematic flux diagram 700. It starts with box 710 when is established that a CoV infect an human and/or a non human subject or population. Once the CoV is identified and characterized the next step 720 is to verify if it both affects mitochondrial function and there is possible to obtain and attenuated CoV that less affects mitochondrial function. This step can be performed for example using the algorithm 600 of FIG. 6 that specifically can return only to results, the attenuated CoV an be obtained or not, however other alternative processes can be used. If such attenuated CoV cannot be obtained then the desired treatment cannot be achieved, the process finishes in step 730 and an alternative solution must be found as treatment. For the purposes of this example method if the original CoV does not affect mitochondrial function is established that the attenuated CoV does not exists and the algorithm goes to 730. In the case the candidate attenuated CoV is obtained the method moves to step 731 wherein the original and the attenuated CoVs are characterized and compared considering their pathological effects in hosts, reproducibility, kinetics, tissue distribution. Several published studies that compare engineered edited CoV with their original wild types often are done with animal models administering viral dosages significantly higher than the natural occurring ones. These studies are often performed on E6 Vero cells from monkeys and/or in small rodents where the CoV viral particles are searched in different organs and tissues after the animals dissection. At the current understanding by attenuating the effect of CoVs on mitochondrial function mitochondrial division is preserved and therefore cell signaling as well as cell cycle may be accelerated and/or even driven to apoptosis. This may result in a diminished release of CoV virons from infected cells and the capability of the immune system to response to them increased compared to the infection by the original CoV. By administering viral loads significantly higher than those common in natural transmission between hosts it can overcame immune host response and may represent infection dynamics and/or transmission rates, but gross virulence characteristics of both CoVs. In most cases this comparison is preclinical and may not involve the testing in human subjects. In step 740 the safety of the candidate CoV is tested, this step may vary depending on the population defined at 710 and/or at 731-740 for testing purposes. For human populations it may involve full phase I studies, for non human ones it can be enough to obtain the results of the previous step 731 and to define safety as relative to the original CoV and therefore to determinate the inclusion of the attenuated CoV in an accepted medical or veterinary formulation. This safety testing involves also determining the adequate safe dosage to be provided to the intended subject or population of step 710. If safety testing fails then the candidate CoV discarded, box 750, and the flow goes back to step 720 to find a new CoV candidate. If the algorithm depicted in 600 is used, it will provide a new attenuated CoV candidate or an indication that the candidate does not exists. In the case of the safety tests 740 succeeded then it is evaluated at step 750 if the candidate CoV prevents the infection by the original CoV at the same population and/or to a representative subject of those depicted at step 710. There are several ways to preform this testing the most commons involve a two stages infection exposition to a number of subjects, first to the attenuated CoV candidate and secondly to the original CoV. Clinical development of human vaccines is a three-phase process. During Phase I, small groups of people receive the trial vaccine. In Phase II, the clinical study is expanded and vaccine is given to people who have characteristics (such as age and physical health) similar to those for whom the new vaccine is intended. In Phase III, the vaccine is given to thousands of people and tested for efficacy and safety. Many vaccines undergo Phase IV formal, ongoing studies after the vaccine is approved and licensed for post market surveillance/confirmatory assessment. In a preferred method to evaluate the prevention of infection rates, the candidate CoV is administered to certain subjects of a population and the infection rates are compared to a control population wherein either none of the subjects was exposed to the candidate CoV or they were exposed to a placebo. This preferred method is of special interest because, contrarily to most common vaccines, the attenuated CoV candidate can infect and spread to more subjects that those who received the doses saving significantly in production and distribution costs. Once the candidate CoV is validated on the target population it can be cleared to be included in an accepted medical or veterinary formulation, depending on the regulation of each country, as a vaccine as shown in step 780. There can be different reasons to a vaccine candidate to fail as for example unexpected mutations or because molecular differences between the original and attenuated CoV. There is then room to ask if the attenuated CoV will serve as treatment for infected subject by the original CoV. This question is done at step 770. There are many steps to validate the candidate CoV as a treatment, some of them may be done already in step 760. Preferred methods include administering the attenuated CoV to infected groups and compare it with placebos or a treatment considered a gold standard. Once the candidate CoV is validated as a treatment for the target population it can be cleared to be included in an accepted medical or veterinary formulation, depending on the regulation of each country, as a treatment as shown in step 790. Following the algorithm 700 it can be obtained one of the following three results in a finite number of steps. 1) an attenuated CoV can be used as a vaccine; 2) an attenuated CoV can be used as a treatment; or 3) is not possible to obtain an attenuate CoV to be used as a vaccine and/or treatment by attenuating its effect on mitochondrial function using gene editing techniques. The method depicted at algorithm 700 is only an example, it is possible between other possibilities to swap between steps 760 and 770 and obtain an attenuated CoV that serves as treatment but not as a vaccine.

Referring to FIG. 8. An simplified algorithm of a preferred method to obtain a vaccine or treatment for an engineered CoV developed as weapon is shown as a schematic flux diagram 800. It starts with box 810 when the weaponized CoV is detected. The following steps 820, 830, 831, 840 and 850 are similar to 720, 730, 731, 740 and 750 from the algorithm depicted at 700 respectively. If the safety tests of step 840 succeeded then it is evaluated at step 860 if the candidate CoV can be used as a treatment. Preferred methods include administering the attenuated CoV to infected groups and compare it with placebos or a treatment considered a gold standard. Once the candidate CoV is validated as a treatment for the target population it can be cleared to be included in an accepted medical or veterinary formulation, depending on the regulation of each country, as an antidote as shown in step 880. If the attenuated CoV is not effective as an antidote then at step 870 is evaluated if it prevents the infection at the same population and/or to a representative subject of those affected of the weapon of step 810. This testing is performed at the same manner as step 760 of algorithm 700 resulting in a vaccine at box 890 or in the discarding of the attenuated CoV candidate at step 850 seconded by a new iteration to find an alternative attenuated CoV candidate at step 82, By following this algorithm always will achieved one of three results in a finite number of steps. 1) an attenuated CoV can be used as an antidote; 2) an attenuated CoV can be used as a vaccine; or 3) is not possible to obtain an attenuate CoV that serves neither as antidote or vaccine for the weapon by attenuating its effect on mitochondrial function using gene editing techniques. The method depicted at algorithm 800 is only an example, it is possible between other possibilities to swap between steps 860 and 870 and obtain an attenuated CoV that serves as vaccine but not as antidote.

Referring to FIG. 9. Maps[3] converted to black and white images of the prevalence of two different mitochondrial haplogroups in Europe, North Africa and West Asia 900 are shown. 910 represent the prevalence of the combined H1 and H3 haplogroups that show some direct correlation with the initial spreading rate of the COVID-19 pandemic and mortality rate. 910 represent the prevalence of the U3 haplogroup that shows some inverse correlation with the initial spreading rate of the COVID-19 pandemic and mortality rate. Even if a first instance these maps appears to be well adjusted to variation on population density and age, they need further research, validation and characterization. There are areas as South Italy, West Russia and Mid Turkey that do not correlate so well with the pandemic evolution. These maps lost accuracy due to black an white conversion compared to the original reference[3] and the original reference should be consulted for more accurate information.

Any of the embodiments described herein may be modified to include any of the structures or methodologies disclosed in connection with different embodiments. Further, the present disclosure is not limited to attenuated coronavirus treatments and vaccines of the type specifically shown.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the objectives are reserved and can be included totally or partially as part of the claims of the definitive patent application of this invention.

The invention claimed is:

1. A method for preventing a condition characterized by impaired mitochondrial function in an animal or human subject, wherein the condition is caused directly or indirectly by the infection with a first coronavirus strain characterized by having in its genome a gene that encodes a molecule that affects mitochondrial function in infected cells; and the method further comprising (a) removing or silencing said gene by a gene editing technique to obtain a mutated second coronavirus strain; and (b) administering the second coronavirus strain to an animal or human subject as part of an accepted medical or veterinary formulation.

2. The method of claim 1 wherein the first coronavirus strain is characterized by having being generated by applying a gene editing technique preceding the steps (a) and (b).

3. The method of claim 1 wherein said removed or silenced gene is the nucleocapsid gene.

4. The method of claim 1 wherein said affecting on mitochondrial function of said first coronavirus strain is more accentuated or intense than that of the mutated second coronavirus strain.

5. The method of claim 1 wherein said second coronavirus strain is able to infect cells and be replicated within the infected cells.

6. The method of claim 1 wherein said prevention of the condition characterized by impaired mitochondrial function involves the treatment of an existing disease.

7. The method of claim 1 wherein said prevention of the condition characterized by impaired mitochondrial function involves the assessment of at least one unit selected from the group consisting of a health condition and disease in said animal or human subject.

8. The method of claim 1 wherein said second coronavirus strain has similar infection or replication rates to those of the first coronavirus strain.

9. The method of claim 1 wherein said molecule is a protein translated from an open reading frame at the nucleocapsid gene.

10. The method of claim 1 wherein the editing technique is performed at the nucleocapsid gene.

11. The method of claim 1 wherein said molecule is a protein translated from an open reading frame.

12. The method of claim 1 wherein said molecule is homologous to a protein translated from the open reading frame 9b from the one of the viruses from the group of SARS-CoV and SARS-CoV2.

13. The method of claim 1 wherein the first coronavirus strain is a natural occurring virus.

14. The method of claim 1 wherein the viral content of said clinical formulation does not exceed 200 plaque forming units.

15. The method of claim 1 wherein the viral content of said clinical formulation does not exceed 100 plaque forming units.

* * * * *